(12) United States Patent
Kunis

(10) Patent No.: US 10,828,475 B2
(45) Date of Patent: Nov. 10, 2020

(54) IMPLANT DEVICE WITH STABLIZER

(71) Applicant: Christopher Gerard Kunis, Escondido, CA (US)

(72) Inventor: Christopher Gerard Kunis, Escondido, CA (US)

(73) Assignee: ASSIST MEDICAL, LLC, Escondido, CA (US)

( * ) Notice: Subject to any disclaimer, the term of this patent is extended or adjusted under 35 U.S.C. 154(b) by 1331 days.

(21) Appl. No.: 14/312,118

(22) Filed: Jun. 23, 2014

(65) Prior Publication Data

US 2014/0379022 A1    Dec. 25, 2014

Related U.S. Application Data

(60) Provisional application No. 61/957,010, filed on Jun. 21, 2013, provisional application No. 61/957,257, (Continued)

(51) Int. Cl.
*A61M 29/00* (2006.01)
*A61F 2/88* (2006.01)
(Continued)

(52) U.S. Cl.
CPC ........... *A61M 29/00* (2013.01); *A61B 5/0422* (2013.01); *A61B 5/686* (2013.01); *A61B 18/14* (2013.01);
(Continued)

(58) Field of Classification Search
CPC ...................................... A61F 2/88; A61F 2/89
See application file for complete search history.

(56) References Cited

U.S. PATENT DOCUMENTS 5,851,232 A * 12/1998 Lois ..................... A61F 2/2412
                                                       623/1.13
8,083,790 B2    12/2011 Lentz et al.
(Continued)

FOREIGN PATENT DOCUMENTS

WO    2010082026    7/2010

OTHER PUBLICATIONS

International Search Report and Written Opinion from related PCT application No. PCT/US14/44292 dated Oct. 15, 2014.
(Continued)

*Primary Examiner* — Michael J D Abreu
(74) *Attorney, Agent, or Firm* — Onello & Mello, LLP

(57) ABSTRACT

Devices and methods are described that can be used to treat various maladies, such as pulmonary vein stenosis hypertension and/or atrial fibrillation. The device may be an implant device having at least one ring and a stabilizer element. In some embodiments, the device can include two or more rings separated by one or more stabilizer element. The ring(s) and at least one stabilizer element provide mechanical pressure against adjacent tissue, e.g., the tissue of a vessel, and the pressure works to inhibit the propagation of the ring to lose position against the wall of said vessel. Methods of implanting the device and methods of treating patients therewith are also provided. Additionally, a delivery apparatus and method may also be provided to deliver such an implant device to a target location within a body, e.g., a vein are artery of a human body.

22 Claims, 11 Drawing Sheets

Related U.S. Application Data filed on Jun. 26, 2013, provisional application No. 61/957,309, filed on Jun. 27, 2013, provisional application No. 61/878,340, filed on Sep. 16, 2013, provisional application No. 61/957,371, filed on Jul. 1, 2013, provisional application No. 61/902,498, filed on Nov. 11, 2013.

(51) Int. Cl.

| | | |
|---|---|---|
| *A61B 5/042* | (2006.01) | |
| *A61B 5/00* | (2006.01) | |
| *A61N 1/05* | (2006.01) | |
| *A61B 18/14* | (2006.01) | |
| *A61F 2/958* | (2013.01) | |
| *A61B 18/00* | (2006.01) | |

(52) U.S. Cl.
CPC ............ *A61F 2/88* (2013.01); *A61N 1/0563* (2013.01); *A61B 2018/00351* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61F 2/958* (2013.01); *A61F 2250/0002* (2013.01); *A61F 2250/0059* (2013.01); *A61M 2205/04* (2013.01)

(56) References Cited

U.S. PATENT DOCUMENTS

| | | |
|---|---|---|
| 2001/0000188 A1 | 4/2001 | Lenker et al. |
| 2002/0065550 A1 | 5/2002 | Smith |
| 2003/0144658 A1 | 7/2003 | Schwartz et al. |
| 2003/0151524 A1 | 8/2003 | Clark |
| 2003/0212449 A1* | 11/2003 | Cox .................. A61F 2/91 623/1.15 |
| 2004/0220655 A1 | 11/2004 | Swanson et al. |
| 2006/0100691 A1 | 5/2006 | St. Germain |
| 2007/0141100 A1 | 6/2007 | Sung et al. |
| 2008/0109076 A1 | 5/2008 | Cartledge et al. |
| 2009/0105807 A1 | 4/2009 | Fischell et al. |
| 2009/0143835 A1 | 6/2009 | Pastore et al. |
| 2010/0004727 A1 | 1/2010 | Andersen et al. |
| 2011/0118818 A1 | 5/2011 | Masters et al. |
| 2011/0282343 A1 | 11/2011 | Kunis |
| 2012/0095499 A1 | 4/2012 | Babkes et al. |
| 2012/0123514 A1 | 5/2012 | Kunis |
| 2012/0277842 A1 | 11/2012 | Kunis |
| 2013/0109987 A1 | 5/2013 | Kunis et al. |
| 2013/0204311 A1 | 8/2013 | Kunis |
| 2013/0245621 A1 | 9/2013 | Persson et al. |

OTHER PUBLICATIONS

International Search Report and Written Opinion from corresponding PCT application No. PCT/US14/43674 dated Oct. 24, 2014.

* cited by examiner

IMPLANT DEVICE WITH STABILIZER

CROSS-REFERENCE TO RELATED APPLICATIONS

This application claims benefit under 35 USC 119(e) of U.S. Provisional Patent application 61/957,010, filed Jun. 21, 2013, entitled "Method and Device for Treatment of Pulmonary Vein Stenosis and Other Maladies;" U.S. Provisional Patent application 61/957,257, filed Jun. 26, 2013, entitled "Device and Method for Treatment of Mammilian Arrhythmias, Neurological Disorders and Other Maladies;" U.S. Provisional Patent application 61/957,309, filed Jun. 27, 2013, entitled "Device and Method for Treatment of Left Atrial Apendage Ligation in Mammilian and Other Maladies;" U.S. Provisional Patent application 61/878,340, filed Sep. 16, 2013, entitled "Device and Method for Treatment of Mammilian Arrhythmias and Neurological Disorders and Other Maladies;" U.S. Provisional Patent application 61/957,371, filed Jul. 1, 2013, entitled "Device and Methods for Implant with Spine and C-ring for Treating a Series of Maladies Within Mammilian Body;" and U.S. Provisional Patent application 61/902,498, filed Nov. 11, 2013, entitled "Implant Device with Spine and C-ring and Method of Making, Delivering, and Using Same", each of which is incorporated by reference herein in their entirety.

FIELD OF INTEREST

The present inventive concepts relate to the field of medical device and treatment, and more particularly to the field of implantable devices useful for keeping previously blocked or narrowed passageways within the body open.

BACKGROUND

Atrial fibrillation (AF) is a common and dangerous disease. It is the most common arrhythmia, and accounts for approximately ⅓ of all hospitalizations due to heart rhythm disorders. In addition, atrial fibrillation ablation patients have a greatly increased risk of pulmonary vein stenosis (narrowing) as a result of energy based therapies, in addition there is a 6× increase stroke mortality.

Current first-line therapies for atrial fibrillation include the use of anti-arrhythmic drugs and anti-coagulation agents. Drugs are useful at reducing symptoms, but often include undesirable side effects. Anti-coagulation agents can reduce the risk of stroke, but often increase the risk of bleeding.

Second-line therapies include surgical and catheter ablation. However, the same are associated with high complication rates, such as pulmonary vein (PV) stenosis, long procedure times, and limited clinical evidence. In addition, their administration typically requires extensive training in the use and installation of complex ablation technology.

Pulmonary vein (PV) isolation is the cornerstone of ablation strategies and these procedures are growing annually. Therefore, the number of complications, such as PV stenosis is also increasing. Additionally, there is a greater need today, more than ever, for a device for the treatment of these complications as well as idiopathic pulmonary fibrosis.

SUMMARY

In accordance with aspects of the inventive concept, provide is an implant device having at least one elongated substrate and at least one stabilizer element (or "implant-stabilizer device"). The implant-stabilizer device may be referred to as a "ribbon," which can take a variety of forms, e.g., a ring or helix. The stabilizer element can extend laterally from the elongated substrate to engage an inner wall of an internal vessel of a body, an artery or vein, as examples. Methods of implanting the device and methods of treating patients therewith are also provided. Additionally, a delivery apparatus and method may also be provided to deliver such an implant device to a target location within a body, e.g., a human body.

In accordance with one aspect of the inventive concepts, provided is an implant device, comprising at least one elongated substrate and at least one stabilizer element laterally extending from the at least one substrate. The at least one elongated substrate and the at least one stabilizer element implant device are configured to radially expand from a compressed to a deployed state.

In various embodiments, the at least one substrate and the at least one stabilizer element can have a helical coil shape.

In various embodiments, the implant device can comprise a plurality of substrates.

In various embodiments, the implant device can comprise a plurality of stabilizer elements.

In various embodiments, the at least one substrate and the at least one stabilizer element can have a ring shape.

In various embodiments, the implant device can comprise a plurality of substrates.

In various embodiments, the plurality of substrates can consist of two ring-shaped substrates separated by an intermediate stabilizer element.

In various embodiments, the implant device can comprise a plurality of stabilizer elements.

In various embodiments, the implant device can be configured to apply a substantially constant radial force against inner walls of a mammalian vessel at a target location in the deployed state.

In various embodiments, the substantially constant radial force can have a magnitude sufficient to dilate the mammalian vessel at the target location.

In various embodiments, the unconstrained diameter of the implant device can be at least 15% greater than a predetermined diameter of the mammalian vessel at the target location.

In various embodiments, the implant device can be configured to deliver a radial force against inner wall tissue of a mammalian vessel at a target location of between about 0.5 g/mm$^2$ and 300 g/mm$^2$ in the deployed state.

In various embodiments, the implant device can be configured to deliver a radial force against tissue of a mammalian vessel at a target location that is sufficient to cause necrosis or apoptosis in the tissue in a deployed state, the necrosis or apoptosis sufficient to or delay electrical, neurological signal conduction traveling along an axis of the vessel and/or within an adjacent chamber in mammalian.

In various embodiments, the implant device can be configured to deliver a radial force against tissue of a mammalian vessel at a target location that is sufficient to compress at least one Ion channel in the adjacent tissue sufficient to delay electrical or neurological signals traveling along an axis of the vessel and/or within an adjacent chamber in mammalian.

In various embodiments, the implant device can further comprise a micro-circuit configured to measure or monitor a value of electrical conduction propagating along the axis of a mammalian vessel within which the implant device is deployed.

In various embodiments, the implant device can further comprise one or more electrodes disposed in or on the at least one substrate and in communication with the micro-circuit, the one or more electrodes configured for sensing conditions within the vessel and/or delivering energy to the vessel.

In various embodiments, the one or more electrodes can include ablation electrodes, mapping electrodes, or ablation and mapping electrodes.

In various embodiments, the micro-circuit can be configured to use an Ionic exchange with the vessel to charge a battery of the micro-circuit.

In various embodiments, the micro-circuit can be configured to measure and/or monitor a value of electrical conduction propagating along the axis of the vessel.

In various embodiments, the micro-circuit can be further configured to wirelessly transmit an indication of the electrical conduction in mammalian.

In various embodiments, the micro-circuit can be configured to receive an electromagnetic signal and to inductively heat the vessel in response to the electromagnetic signal.

In various embodiments, the at least one stabilizer element can be at least one wire. The at least one wire can be formed in a zigzag pattern.

In accordance with another aspect of the inventive concepts, provided is a method for treating a malady in a mammalian, comprising determining a radial diameter of a vessel of a mammalian; providing an implant device having an unconstrained radial diameter that is greater than a radial diameter of a target location of the vessel; delivering the implant device to the target location; and expanding the implant device at the target location, thereby dilating the vessel at the target location. The implant device comprises at least one elongated substrate and at least one stabilizer element laterally extending from the at least one substrate, wherein the at least one elongated substrate and the at least one stabilizer element implant device are configured to radially expand from a compressed to a deployed state.

In various embodiments, the at least one substrate and the at least one stabilizer element can have a helical coil shape.

In various embodiments, the implant device can comprise a plurality of substrates.

In various embodiments, the implant device can comprise a plurality of stabilizer elements.

In various embodiments, the at least one substrate and the at least one stabilizer element can have a ring shape.

In various embodiments, the implant device can comprise a plurality of substrates.

In various embodiments, the plurality of substrates can consist of two ring-shaped substrates separated by an intermediate stabilizer element.

In various embodiments, the implant device can comprise a plurality of stabilizer elements.

In various embodiments, the method can further include the implant device applying a substantially constant radial force against inner walls of a mammalian vessel at a target location in the deployed state.

In various embodiments, the unconstrained diameter of the implant device is at least 15% greater than the radial diameter of the mammalian vessel at the target location.

In various embodiments, the method can further comprise the implant device delivering a radial force against inner wall tissue of a mammalian vessel at a target location of between about 0.5 g/mm$^2$ and 300 g/mm$^2$ in the deployed state.

In various embodiments, the method can further comprise the implant device delivering a radial force against tissue of a mammalian vessel at a target location that is sufficient to cause necrosis or apoptosis in the tissue in a deployed state, the necrosis or apoptosis sufficient to or delay electrical, neurological signal conduction traveling along an axis of the vessel and/or within an adjacent chamber in mammalian.

In various embodiments, the method can further comprise the implant device delivering a radial force against tissue of a mammalian vessel at a target location that is sufficient to compress at least one Ion channel in the adjacent tissue sufficient to delay electrical or neurological signals traveling along an axis of the vessel and/or within an adjacent chamber in mammalian.

In various embodiments, the implant device can further comprise a micro-circuit, and the method can further comprise using the micro-circuit, measuring and/or monitoring a value of electrical conduction propagating along the axis of a mammalian vessel within which the implant device is deployed.

In various embodiments, the implant device can further comprise one or more electrodes disposed in or on the at least one substrate and in communication with the micro-circuit, and the method can further comprise the one or more electrodes sensing conditions within the vessel and/or delivering energy to the vessel.

In various embodiments, the one or more electrodes can include mapping electrodes, and the method can further comprise mapping activity or geometry of a chamber associated with the vessel.

In various embodiments, the one or more electrodes can include ablation electrodes, and the method can further comprise ablating tissue at the target location.

In various embodiments, the method can further comprise the micro-circuit using an Ionic exchange with the vessel to charge a battery of the micro-circuit.

In various embodiments, the method can further comprise the micro-circuit measuring and/or monitoring a value of electrical conduction propagating along the axis of the vessel.

In various embodiments, the method can further comprise the micro-circuit wirelessly transmitting an indication of the electrical conduction in mammalian.

In various embodiments, the method can further comprise the micro-circuit receiving an electromagnetic signal and in response inductively heating the vessel at the target location.

In accordance with another aspect of the inventive concepts, provided is an implant kit, comprising A kit for treating a malady by deploying an implant device in a vessel or chamber, comprising: an implant device structured and configured for implantation into a mammalian pulmonary vein, the device configured to exert a pressure against a region including the ostium, such that the implantation of the device provides that the pressure against the region including the ostium is substantially consistently greater than zero; and a delivery system, such that upon deployment from the delivery system, the implant device is disposed within a target vessel.

In various embodiments, the delivery system can include a catheter with a distal section at a distal end thereof.

In various embodiments, the implant device is a ring-shaped device having one or more rings and at least one laterally extending stabilizer element, the ring-shaped device having at least one winding.

In accordance with another aspect of the inventive concepts, provided is a kit for treating a malady by deploying an implant device in a vessel, comprising: a device structured and configured for implantation into a mammalian pulmonary vein; and a delivery device for implanting and allowing manipulation of the implanted device, the implanted device for treating a malady, the delivery device comprising a catheter including a delivery lumen, the delivery lumen extending from a catheter proximal end, the catheter further comprising a distal section through which the delivery lumen extends, the distal section being collinear with the catheter during delivery and configurable into a semi-circular pattern during deployment of the implanted device.

In accordance with another aspect of the inventive concepts, provided is a delivery device for intra-operatively delivering an implant for treatment of atrial fibrillation, comprising a catheter having a distal portion configured to hold an implant device in an un-deployed state. The implant device comprises at least one substrate and at least one laterally extending stabilizer element.

In accordance with another aspect of the inventive concepts, provided is a method for intraoperative treatment of atrial fibrillation, comprising: during an open-heart surgery, implanting an implant device into a pulmonary vein or chamber, the implanted device oversized and thus configured to exert a pressure against the tissue region including the ostium and a portion of the pulmonary vein, such that the implantation provides that the pressure against the region including the ostium and a portion of the pulmonary vein is substantially consistently greater than zero. The implant device comprises at least one substrate and at least one laterally extending stabilizer element.

In accordance with another aspect of the inventive concepts, provided is a method for determining propriety of implant installation configuration prior to release from a delivery device, the implant for treatment of pulmonary vein stenosis, hypertension and or atrial fibrillation, comprising: detecting a first level of vessel narrowing, conduction pathway within a pulmonary vein; implanting a device at least partially into the pulmonary vein or chamber through a delivery device, the implanted device oversized and thus configured to exert a pressure against the region including the ostium and a portion of the pulmonary vein, the device to be implanted coupled to a pusher wire, the pusher wire configured to force the device through the delivery device and at least partially into the pulmonary vein; detecting a second level of conduction along a pulmonary vein; if the second level is sufficiently below the first level, causing the device to separate from the pusher wire; if the second level is not sufficiently below the first level, using the pusher wire to change the position of the device at least partially within the pulmonary vein.

In accordance with another aspect of the inventive concepts, provided is a method for determining propriety of implant installation configuration prior to release from a delivery device, the implant for treatment of pulmonary vein stenosis, hypertension and or atrial fibrillation, comprising: implanting a device at least partially into the pulmonary vein through a delivery device, the implanted device oversized and thus configured to exert a pressure against the region including the ostium and a portion of the pulmonary vein, the device to be implanted coupled to a pusher wire or other deliver system options, the pusher wire configured to force the device through the delivery device and at least partially into the pulmonary vein; detecting an orientation of the implanted device relative to the pulmonary vein; if the orientation of the implanted device is appropriate relative to the pulmonary vein, causing the device to separate from the pusher wire; if the orientation of the implanted device is not appropriate relative to the pulmonary vein, using the pusher wire to change the position of the device at least partially within the pulmonary vein.

In various embodiments, the implant device includes a proximal ring, a distal ring, and stabilizer element between the proximal and distal ring, and wherein the orientation is determined to be appropriate if the rings are perpendicular to the axis of the pulmonary vein or within 30° of being perpendicular to the axis of the pulmonary vein.

In various embodiments, the method further comprises using fluoroscopy to determine the orientation of the implanted device and patency of a vessel.

In accordance with another aspect of the inventive concepts, provided is a device for determination of post-implantation vessel patency and electrical conduction parameters, comprising: at least one ring and stabilizing element, the at least one helical ring including a flexible circuit including a receiver for reception of signals corresponding to electrical conduction in a pulmonary vein; a transmitter, the transmitter for transmitting a wireless signal indicative of the received signals.

In various embodiments, the receiver is the at least one helical ring.

In various embodiments, the transmitter is configured to transmit two types of signals, a first type of signal corresponding to sinus rhythm, and a second type of signal corresponding to non-sinus rhythm.

In various embodiments, the second type of signal corresponds to atrial fibrillation.

In accordance with another aspect of the inventive concepts, provided is a method for determination of post-implantation electrical conduction parameters, comprising: implanting at least one ring in a pulmonary vein, the at least one ring including a flexible circuit including a receiver for reception of signals corresponding to electrical conduction in a pulmonary vein, the flexible circuit further comprising a transmitter for transmitting a wireless signal indicative of the received signals; receiving a signal transmitted wirelessly from the transmitter, and rendering a result corresponding to the received signal on a display.

In various embodiments, the result indicates sinus rhythm or non-sinus rhythm.

In accordance with another aspect of the inventive concepts, provided is a method for treating a malady, comprising: inserting an implant device into a vessel of the patient, the vessel substantially defining a longitudinal axis, the implant device including a proximal ring substantial defining a proximal plane, a distal ring substantially defining a distal plane, and stabilizing element connecting the proximal ring to the distal ring; such that the inserting includes inserting the implant device such that a proximal angle between the proximal plane and the longitudinal axis is 90 degrees plus or minus 30 degrees, and such that a distal angle between the distal plane and the longitudinal axis is 90 degrees plus or minus 30 degrees.

In various embodiments, the method can further comprise measuring the angle of the rings using fluoroscopy.

In various embodiments, the malady is atrial fibrillation and the vessel is a pulmonary vein, the method further comprising measuring a first value of the electrical conduction along the pulmonary vein prior to the inserting, and measuring a second value of the electrical conduction along the pulmonary vein subsequent to the inserting, and if the second value is not sufficiently below the first, then performing one or more of the below steps: installing a touchup ring into the pulmonary vein; re-inserting the implant device into the pulmonary vein or chamber within a mammalian; performing a step of ablating the pulmonary vein wherein the ablating is performed using RF or cryoablation; or inductively heating the implant device to cause necrosis or apoptosis of adjacent tissue.

In accordance with another aspect of the inventive concepts, provided is a delivery device for implanting and allowing manipulation of an implant, the implant for treating a malady, the delivery device comprising: a catheter including a delivery lumen, the delivery lumen extending from a catheter proximal end to a catheter distal end; a pusher configured for insertion into the delivery lumen, the pusher including a distal end, the distal end of the pusher including a device for securing an implant, the device for securing an implant including a universal joint, the universal joint allowing no additional degrees of freedom when the universal joint is within and not adjacent to the catheter distal end, the universal joint allowing two additional degrees of freedom when the universal joint is outside of or adjacent to the catheter distal end.

In various embodiments, the pusher further comprises a wire attachable to the implant.

In various embodiments, the delivery lumen is configured to allow placement of at least two pushers and respective implants therein.

In various embodiments, the delivery lumen is configured to allow placement of a cartridge therein, the cartridge containing at least two implants.

In various embodiments, the catheter distal end further comprises electrodes for RF ablation or mapping.

In various embodiments, the catheter is configured to provide RF ablation or mapping through the implant.

In accordance with another aspect of the inventive concepts, provided is a delivery device for implanting and allowing manipulation of an implant, the implant for treating a malady, the delivery device comprising: a catheter including a delivery lumen, the delivery lumen extending from a catheter proximal end; the catheter further comprising a distal section through which the delivery lumen extends, the distal section being straight and collinear with the catheter during delivery and configurable into a circular shape during deployment of the implant.

In various embodiments, the distal section is located at a distal end of the catheter.

In various embodiments, the distal section is located proximal to a distal end of the catheter.

In various embodiments, a radial size of the distal section is adjustable using a lever or knob on a handle of the catheter, the handle located at a proximal end of the catheter.

In various embodiments, a maximum radial size of the distal section is configured to be 5 mm or 25 mm.

In various embodiments, the catheter and distal section are configured such that deployment of the implant in a vessel leads to an axis of the implant being substantially parallel to an axis of the vessel, wherein substantially parallel is between about 0 and 30°.

In various embodiments, the distal section further comprises electrodes for RF ablation or mapping.

In various embodiments, the catheter configured to provide RF ablation or mapping through the implant.

In accordance with another aspect of the inventive concepts, provided is a method for treating a malady, comprising: Inserting an implant into a delivery lumen of a delivery device, the implant including at least one ring when delivered, the ring associated with a twist direction, the delivery device including a proximal end and a distal end; disposing the distal end of the delivery device at a delivery location; pushing the implant through the delivery lumen using a pushing device coupled at a distal end of the pushing device to the implant; pushing the implant such that the implant exits the distal end of the delivery device but is still attached to the delivery device.

In various embodiments, the helical ring is formed of a ribbon having a width greater than the thickness of said ribbon.

In various embodiments, the delivery location is a mammalian pulmonary vein.

In various embodiments, the pushing device includes a universal joint, the universal joint configured to allow two degrees of freedom when the distal end of the pushing device is distal to or adjacent the distal end of the delivery device, the two degrees of freedom not including an azimuthal rotation angle associated with the twist.

In various embodiments, the angular amount is between about 3-5%.

In accordance with another aspect of the inventive concepts, provided is a method for assisting patency of a vessel, comprising implanting a device at least partially into a vessel through a delivery device, the device including a proximal ring, a distal ring, and stabilizing element between the proximal and distal ring, and wherein the implanting is such that the rings are perpendicular to the axis of the vessel or within 30° of being perpendicular to the axis of the vessel.

In accordance with another aspect of the inventive concepts, provided is a method for treating atrial fibrillation, comprising implanting a device at least partially into a left atrial substrate of a patient through a delivery device, the device including a proximal ring, a distal ring, and stabilizing element between the proximal and distal ring, and wherein the implanting is such that the rings are inner locked to form a ring after deployment and unclosed ring prior to and during deployment into said vessel.

In accordance with another aspect of the inventive concepts, provided is a method for treating hypertension, comprising implanting a device at least partially into a renal vein through a delivery device, the device including a proximal ring, a distal ring, and stabilizing element between the proximal and distal ring, and wherein the implanting is such that the rings are perpendicular to the axis of the vein or within 30° of being perpendicular to the axis of the vein.

In accordance with another aspect of the inventive concepts, provided is a method for treating a malady, comprising: choosing a size of an implant device for insertion into a vessel of a patient, the implant device including a proximal ring, a distal ring, and stabilizing element connecting the proximal ring to the distal ring or to a single ring; and inserting the implant device into the vessel of the patient, such that the choosing includes selecting a size of the distal ring of the implant device to be about 15-50% oversized compared to the size of the vessel.

In various embodiments, the method further comprises selecting a size of the distal ring of the implant device to be about 10-45% oversized compared to the size of the vessel.

In various embodiments, the method further comprises selecting a size of the distal ring of the implant device to be about 10-40% oversized compared to the size of the vessel.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION

Figure 1:
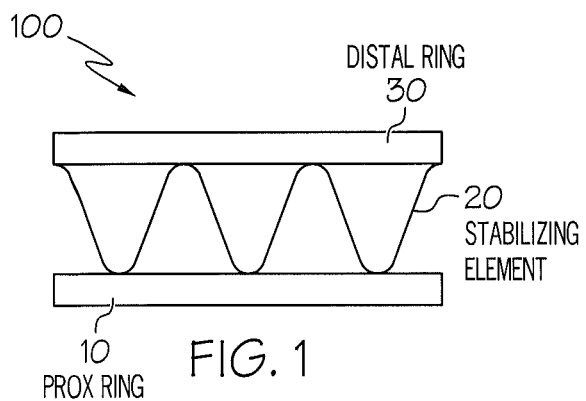
FIG. 1 is an embodiment of a single-substrate implant device with stabilizer element, according to aspects of the inventive concept.

Various aspects of the inventive concepts will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

Exemplary embodiments are described herein with reference to cross-sectional illustrations that are schematic illustrations of idealized exemplary embodiments (and intermediate structures). As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

In accordance with aspects of the inventive concept, provide is an implant device having a stabilizer element. Methods of implanting the device and methods of treating patients therewith are also provided. Additionally, a delivery apparatus and method may also be provided to deliver such an implant device to a target location or vessel within a body, e.g., a vein or artery of a human body.

In accordance with aspects of the inventive concepts, devices and methods can be provided that are especially suited for treating complications of AF ablation patients. For example, such treatment can be by means of surgical, percutaneous or other approaches for placement of an implant device in a vessel passageway, e.g., within a vein for treating pulmonary vein stenosis. As one example, atrial fibrillation for paroxysmal patients and/or patients who have failed a previous radio frequency (RF) ablation where micro-reentrant signals have propagated are candidates for such procedure and implant device.

The present implant device and methods for use relate to an implant device that can improve the safety profile of ablation techniques and offer an optimal solution for treatment of said complications. Therapy is delivered within the vessel having a focal tissue effect sufficient to improve the patency of the vessel, while providing electrically inert tissue to reduce the need for additional ablation procedures that may further damage or stenos vessels. The implant device includes the stabilizer element to maintain stability within the vessel at the point of contact affecting only the implant deployment location, e.g., where ectopic beats occur within the sleeve of the pulmonary vein. No external energy source or capital investment is required for use with the implant device. For example, the stabilizer element can laterally protrude from a side or edge of at least one elongated substrate, wherein the stabilizer element eliminates or substantially eliminates tipping of the device within the vessel.

Unlike some prior devices, the implant device and method need not directly integrate into the wall surface of the pulmonary vein (PV) to obtain isolation, nor is it necessary to cause injury or damage to the tissue via any means of cutting or scoring of atrial or PV cardiac tissue. Rather, in an acute treatment, the implant device is formed to apply and maintain radial and longitudinal stretch or substantially radial force to stretch the vessel tissue along the circumference of the PV, preferably at the ostium, to improve the patency of said vessel, as well as distal/proximal to the ostium via means of the stabilizing element(s).

In various embodiments, the stabilizer element can have a zigzag pattern or shape connecting one or more radially formed elongated substrates (e.g., rings), to improve patency of a vessel. Here, a zigzag pattern can be any pattern or profile having peaks and valleys, including, but not limited to, a sinusoidal pattern or other curved pattern, a saw tooth pattern, a square wave pattern, and the like. In other embodiments, the stabilizer element could be a mesh or series of lateral protrusions extend from at least on substrate.

Embodiments of the implant device and method can be configured to treat pulmonary vein stenosis and may be helpful in maintaining efficacy of ablated patients undergoing hypertension or atrial fibrillation ablation procedures without requiring the delivery of energy, employing needles or other penetrating elements, and without employing elements for scarring. Rather, the implant device provides mechanical energy against cardiac tissue, e.g., against the intimal lining of the PV, improving hemodynamic flow, eliminating the electrical refractory process of the myocytes and inhibiting a chemical reaction at the focal site of the implant, thus rendering the tissue electrically inert—all in one device.

In accordance with one aspect of the inventive concepts, provided is an implant device that can be used to treat a variety of types of maladies. The implant device includes an elongated substrate and a stabilizer element. Such implant device can take the form of a ribbon wrapped or wound around a central axis to take a ring or helical shape.

In various embodiments, the stabilizer element protrudes laterally from the substrate and can have a zigzag pattern to stabilize the substrate and, therefore, the implant device. For example, the stabilizer element can include one or more wires having a zig-zag shape. In various embodiments, the substrate can have a cross-sectional shape different from the stabilizer element, for example, a zigzag wire type of stabilizer element.

In various embodiments, the substrates can take the form of an elongated strip of resilient material that is a length (l) that it is greater than its width (w). The substrate can be flat and thin, having a thickness (t) smaller than its length and width, in some embodiments. In some embodiments, a substrate can take the form of a ring or helical coil. In some embodiments, the implant device can include one, two, or more of such substrates and one, two, or more stabilizer elements.

In various embodiments, an implant device can include multiple substrates in the form of rings. The multiple rings can include a proximal ring and a distal ring. The radius of the proximal ring can be greater than the radius of the distal ring, in some embodiments. In an un-deployed configuration, the radius of the proximal ring may be between about 3 to 60 mm and the radius of the distal ring may be between about 4 to 60 mm. In a deployed configuration, the radius of the proximal ring may be between about 2 to 40 mm and the radius of the distal ring may be between about 4 to 40 mm.

In some embodiments, the distal ring and the proximal ring can have the same thickness. In other embodiments, the distal ring and the proximal ring can have different thicknesses, e.g., the proximal ring can have a lesser thickness than the distal ring or vice versa. In some embodiments, the distal ring and the proximal ring can have the same width or different widths, e.g., the proximal ring can have a lesser width than the distal ring or vice versa. A width of the ribbon may be significantly larger than the thickness of said ribbon.

The rings may be configured to deliver a force against adjacent tissue when deployed of between about 0.5 g/mm$^2$ and 300 g/mm$^2$, e.g., between about 1 g/mm$^2$ and 200 g/mm$^2$, in various embodiments. In some embodiments, the proximal ring can be configured to deliver a lesser force when deployed against adjacent tissue than the distal ring.

In some embodiments, an extremity of the ring may be shaped to increase frictional or mechanical resistance against movement, e.g., may be shaped to include a zig-zag pattern, scallops, ribs, or a club-shaped end.

In some embodiments, the implant device may be coated with a material composition, surface treatment, coating, or biological agent and/or drug.

In accordance with another aspect of the inventive concepts, provided is an implant kit comprising components useful to treat a malady. The kit can include an implant device as described herein and a delivery system or apparatus. The delivery system can be used to deploy an implant device to a target location within a vessel of a mammalian, according to a method of treatment. The delivery system can include a catheter having a distal end configured to maintain the implant device until delivered to the target location within the vessel of the body—where it can then be deployed. Upon deployment of the implant-stabilizer device from the distal end, a longitudinal axis of the implant device is substantially collinear with a longitudinal axis of the vessel.

In accordance with another aspect of the inventive concept, provided is a method of treating a malady in mammalian. The malady may be PV stenosis, hypertension, atrial fibrillation or vessel non-patency, as examples. The method can utilize the implant device and delivery system in accordance with the inventive concepts. The method can include: measuring a length and diameter of a vessel in a mammalian patient, and choosing a size of an implant device for insertion into the vessel; using the delivery system, delivering the implant device to the target location; deploying the implant device; and withdrawing the delivery system. The implant device can include a proximal ring, a distal ring, and stabilizing element connecting the proximal ring to the distal ring, in some embodiments. In other embodiments, the implant device can include one ring connected to a stabilizing element. The stabilizer element can be configured in a zigzag radial pattern or other patterns for the purposes of stabilizing the implant during deployment and after deployment. The implant device is configured to take a compressed stated for deployment and then, at deployment, to radially dilate to the wall of said vessel along the axis of the vessel. Thus, the size of the implant device can be chosen so that it not only fits in the vessel in the compressed state for deployment, but also exerts a sufficient amount of pressure against the vessel walls to secure its location in post-deployment usage. Thus, as stated above, the rings may be configured to deliver a force against adjacent tissue when deployed of between about 0.5 g/mm$^2$ and 300 g/mm$^2$, e.g., between about 1 g/mm$^2$ and 200 g/mm$^2$, in various embodiments.

The delivering step may include delivering the implant device to the vessel through or exterior to a catheter including a distal end. The vessel can be a pulmonary vein or renal artery. The method may further include mapping at least one pulmonary vein and/or ablating at least one pulmonary vein. The ablating may be performed using at least one electrode disposed on a delivery device. The inserting may include delivering the distal ring into the pulmonary vein and delivering the proximal ring into the ostium of a pulmonary vein. The method may further include administering local anesthesia and not general anesthesia to the patient. The delivering step may further include pushing the implant device through a lumen of the catheter with a pushing mechanism or device. The pushing mechanism or device may be coupled to the implant device using a grabbing mechanism.

The mapping may include determining the sizes of at least two pulmonary veins, and may further include delivering at least one implant device to each pulmonary vein. The mapping may be performed before and/or after inserting the implant device.

The method may further include loading more than one implant device into or onto the delivery device in the order in which they are to be successively implanted in pulmonary veins, so that multiple implant device deliveries can be done in a single entry into the body. The method may further include recapturing or removing the implant device after the delivery.

The method may further include inducing a local heating effect to be present on the implant device by induction to aid in maintaining the patency of said treated vessel. The implant device can be sized and configured to compress a wall of a vessel, nerve or nerve bundles, Ion channel(s) in adjacent tissue sufficient to block or retard signals traveling along the axis of the vessel. This may include compressing the first one to five cellular layers of the adjacent tissue. The compression may be such that the delay is caused in conduction of at least 10%.

In accordance with another aspect of the inventive concepts, provided can be a method for treating a malady of a patient, including: choosing a size of an implant device for insertion into a vessel of a patient, the implant device including a proximal ring, a distal ring, and stabilizing member connecting the proximal ring to the distal ring or connected to a single ring; inserting the implant device into the vessel of the patient, such that the choosing includes selecting an un-deployed or uncompressed radius of the distal ring of the implant device to be at least two times the radius of the vessel.

Various embodiments may include one or more of the following. The method may further include selecting an un-deployed or uncompressed radius of a distal ring of the implant device to be at least five times the radius of the vessel. The implant device may also include micro-circuits or electrical components, such as electrodes, diodes and capacitors etc., e.g., for monitoring vital characteristics of a patient, treating the patient, and/or diagnosing a condition of the patient.

In accordance with another aspect of the inventive concept, provided is a method for treating a malady of a mammalian patient, including: inserting a catheter into a vessel of the patient, the catheter having loaded within an anchoring device for partial insertion into a vessel of the patient, the anchoring device including at least one distal ring; partially extending the distal ring from the catheter such that the distal ring is anchored in the vessel; activating at least one electrode on the catheter, the at least one electrode substantially adjacent to tissue when the distal ring is anchored in the vessel, the activating causing ablation and necrosis of the adjacent tissue or fibrosis; retracting the distal ring into the catheter; and withdrawing the catheter.

Various embodiments in accordance with the inventive concepts can include one or more of the following. The method may further include activating a circuit or plurality of electrodes on the implant device or catheter or both, the electrodes distributed along the implant device or catheter. The method may further include rotating the catheter at least partially during the activating, thereby causing deployment of said implant into tissue. The method may further include inserting the implant device into the vessel. The implant device can include a proximal ring, a distal ring, and stabilizing element between the proximal and distal ring or attached to a single ring.

Advantages of the invention can include one or more of the following. The device can be deployed into a target zone, e.g., into the PV, where cryo-ablation and radio frequency ablation techniques cannot be deployed. Devices may be employed to provide multiple locations of the PV to dissociate ectopic beats that emulate from within the PVs. An implant device in accordance with aspects of the inventive concepts can be delivered using a procedure under only local anesthesia, rather than requiring general anesthesia, in various embodiments.

Implant Device Embodiments

In various embodiments, the implant device can include at least one substrate having a laterally extending stabilizer element. The stabilizer element can be formed from one or more patterned wires. The substrate can take the form of one or more elongated substrates. At least one stabilizer element can be connected between multiple substrates. In some embodiments, the stabilizer element can be connected to one or more substrates in the form of rings. In other embodiments, the stabilizer element can be connected to one or more substrates in the form of a helical coil. The connected substrate(s) and stabilizer element(s) can be formed in a ring shape of a helical shape.

FIGS. 1-4 show various embodiments of an implant device according to aspects of the inventive concepts. In some embodiments, the ring(s) and stabilizer element(s) can be different components connected together by a mechanical or chemical bond. In other embodiments, a flat implant device comprising ring(s) and stabilizer element(s) can be cut out of a sheet of material as a single unit, e.g., laser cut out of a thin, biocompatible material, and then shaped, e.g., into a ring or helical shape. Nitinol may be employed as a material for the rings.

Referring to FIG. 1, an embodiment of an implant device 100 is illustrated schematically. In this embodiments there are two substrates, referred to as a proximal ring 10 and a distal ring 30, which are connected together by a stability element 20 formed of a wire having a zigzag pattern. The stability element 20 also maintains the rings are a predetermined distance from each other. The proximal and distal rings 10, 30 can be each connected to the stability element 20 at various points, e.g., as shown. Each of rings 10, 30 can be a relatively flat band laterally connected to different points of the stabilizer element 20. In some embodiments, rings 10, 30 are maintained substantially in parallel by the stabilizer 20. In other embodiments, the rings 10, 30 could have a lateral distance between them that is not constant. For example, the distance between the rings 10, 30 could get wider and/or smaller over the length of the implant device 100. Exemplary values for a width of each ring can be, e.g., in a range of about 0.5 and 2.5 mm, e.g., between 1-2 mm.

Figure 2:
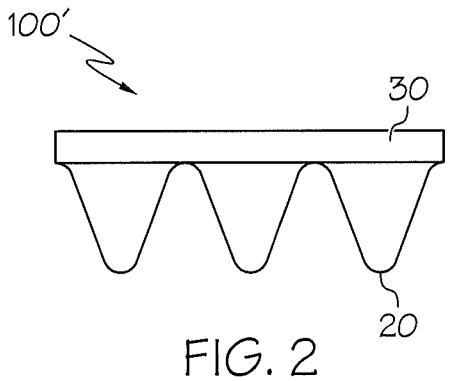
FIG. 2 is an embodiment of a multi-substrate implant device with stabilizer element, according to aspects of the inventive concept.

FIG. 2 shows an embodiment of an implant device 100' having a single ring configuration, rather than the double ring configuration of FIG. 1. In this embodiment, a single ring 30 is employed with a laterally attached stabilizing element 20. The stabilizer element 20 extends from one side of the ring 30, and can be attached at several locations throughout the length of the ring 30, only a portion of which is shown in FIG. 2.

In other embodiment, one or more stabilizer elements 20 could similarly extend from both sides of the ring 30.

Figure 3:
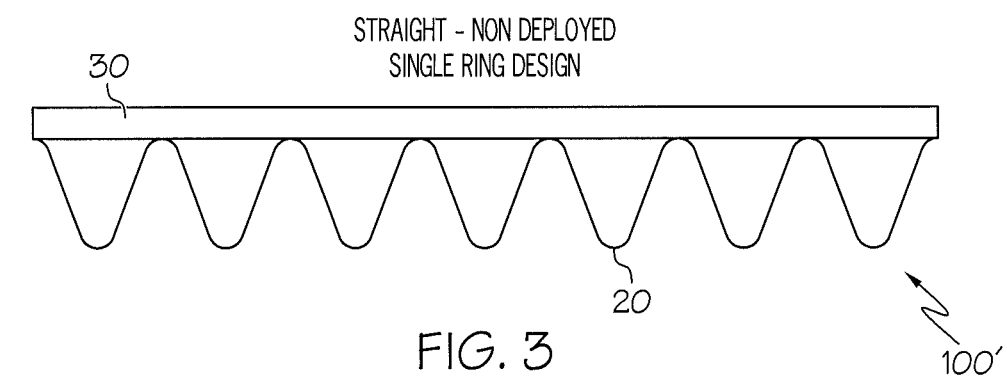
FIG. 3 is an embodiment of a single-substrate implant device with stabilizer element in a straightened arrangement, according to aspects of the inventive concept.

Referring to FIG. 3, illustrated is an embodiment of the implant device 100' of FIG. 2 in a flat, unconstrained or uncoiled form, comprising a single ribbon ring 30 and stabilizer element 20. Here, the implant device 100' is shown in a relatively straight form, but in various embodiments the implant device 100' has a pre-deployment state of having a ring or helical shape, as examples. For instance, the implant device 100' may be formed as a straight workpiece, and then shaped into a ring or helical shape. Once shaped into a predetermined shape, the coiled implant device 100' can be compressed for deployment to a target location within a vessel and then uncompressed or unconstrained so that it expands against inner walls of the vessel to take its deployed state.

Figure 4:
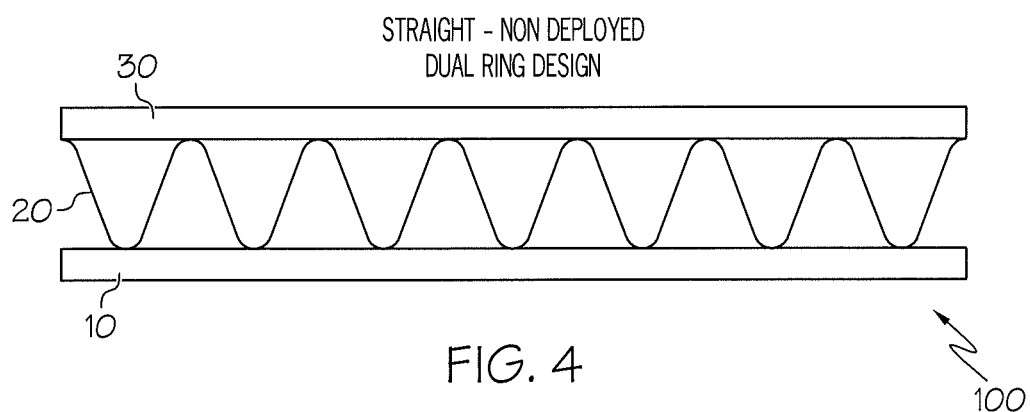
FIG. 4 is an embodiment of a multi-substrate implant device with stabilizer element in a straightened arrangement, according to aspects of the inventive concept.

Referring to FIG. 4, illustrated is an embodiment of the implant device 100 of FIG. 1 in a flat, unconstrained or uncoiled form, with a double ring 10, 30 and stabilizer element 20 configuration. Here, the implant device 100 is shown in a relatively straight form, but in various embodiments the implant device 100 can have a pre-deployment state of having a ring or helical shape, as examples. For instance, the implant device 100 may be formed as a straight workpiece, and then shaped into a ring or helical shape. The coiled implant-stabilizer device 100 can be compressed for deployment to a target location within a vessel and then uncompressed or unconstrained so that it expands against inner walls of the vessel to take its deployed state.

The distal and proximal rings can have the same un-deployed diameter or different un-deployed diameters. In various embodiments, the un-deployed diameter of the proximal ring can be less than the un-deployed diameter of the distal ring, or vice versa. In various embodiments, a diameter of un-deployed proximal ring 10 can be in a range of about 4 mm to 50 mm and a diameter of un-deployed distal ring 30 can be in a range of about 6 mm to 60 mm.

The distal and proximal rings can have the same deployed diameter or different deployed diameters. In various embodiments, the deployed diameter of the proximal ring can be less than the deployed diameter of the distal ring, or vice versa. The diameter can be in a range of about 2 mm to 40 mm for the deployed proximal ring 10, and the diameter can be in a range of about 3 mm to 40 mm for the deployed distal ring 30.

The rings 10, 30 may be configured in a symmetrical pattern, e.g., the diameter of the distal ring 30 may be substantially equal to the diameter of the proximal ring 10, in some embodiments. Alternatively, in other embodiments, an asymmetric pattern may be employed with one ring having a larger or smaller diameter then the other ring, e.g., a distal ring may have a 15 mm diameter while the proximal ring may have a larger 25 mm diameter. Using these values, the rings when un-deployed may be significantly oversized compared to the vessels for which they are intended. They may be, e.g., oversized by 10-100%, e.g., 20-60%, and good results have been seen also for values of 45-55%, e.g., 50% oversizing.

One or both of the rings 10, 30 can be configured to deliver a force against the tissue of inner wall of the vessel of between about 0.5 g/mm$^2$ and 300 g/mm$^2$, e.g., between about 1 g/mm$^2$ and 200 g/mm$^2$. The distal ring 30 can provide a greater amount of force than the proximal ring 10, in some embodiments.

Figure 5:
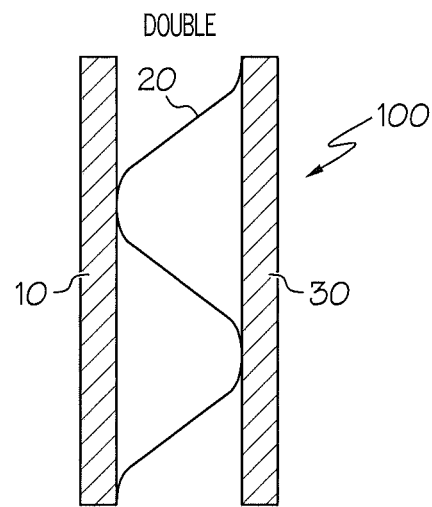
FIG. 5 is an embodiment of a multi-substrate implant device with stabilizer element, according to aspects of the inventive concept.

FIG. 5 shows a side view of the implant-stabilizer device 100 shown in a ring (or double ring) form. Here, rings 10 and 30 are maintained substantially in parallel by an intermediate, laterally protruding stabilizer 20.

Figure 6:
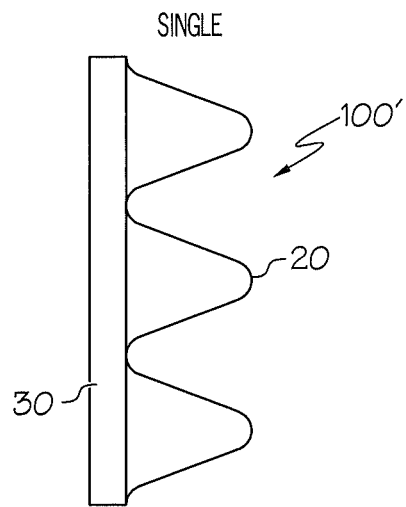
FIG. 6 is an embodiment of a single-substrate implant device with stabilizer element in a straightened arrangement, according to aspects of the inventive concept.

FIG. 6 shows a side view of the implant device 100 shown in a ring (single ring) form. Here, stabilizer element 20 laterally extends from ring 30.

Figure 7:
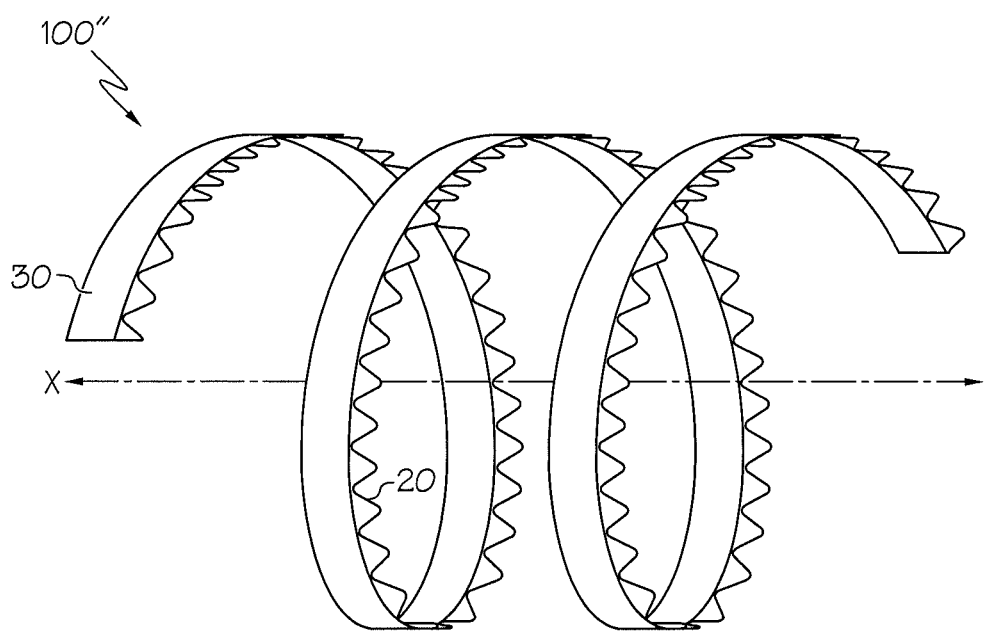
FIG. 7 is an embodiment of a single-substrate implant device with stabilizer element in a helical arrangement, according to aspects of the inventive concept.

FIG. 7 shows an embodiment of an implant stabilizer device 100" in a helical form. This shape may formed by revolving the ring 30 and stabilizer element 20 around a central axis "X", e.g., 1, 1.5, 2, 3, or more times. In this way, even when placed in larger veins, the available expansion room may cause an effective pressure to affix the implant to vessel. However, in this regard, it is noted that radial force decreases dramatically as the radius increases. For example, implant device 100' from FIG. 3 could be shaped into a helical form, as shown in FIG. 7.

Implant device 100" with double rings could take a helical form. For example, implant device 100 from FIG. 4 could be shaped into a helical form, as shown in FIG. 7.

It is noted that limiting migration is assisted by the shape and structure of the implant device. In particular, the overall helical structure of the implant device ensures that a longitudinal force, along the axis of the device, tends to be absorbed by a compression of the helix, similar to the way in which a spring compresses, although the construction ensures that the spring constant may be extremely low, especially in the axial direction. This may be contrasted with other more stent like structures, which are designed such that a longitudinal force is transmitted along the typical chain link or honeycomb structure, causing translation or a change of radius of such structures rather than compression.

Figure 8A:
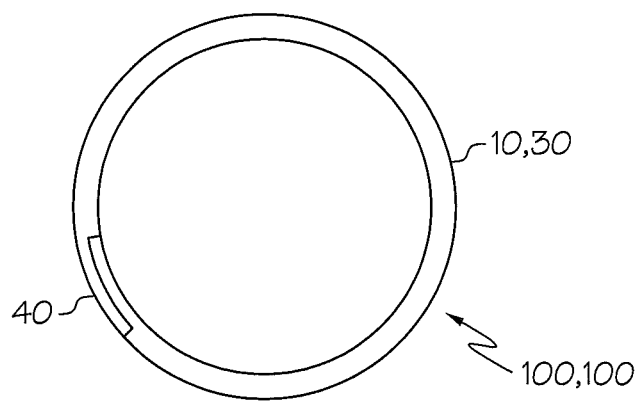
FIG. 8A shows a front view of an embodiment of an implant device with stabilizer element having an overlap, according to aspects of the inventive concept.

In the multi-ring embodiments, there may be various approaches to closing the ring once deployed. In various embodiments, in the deployed state, the ends of the ring(s) may overlap, but in other embodiments they may need overlap. Therefore, the ends of the ring(s) can take various forms, e.g., taper or lapped, scalloped, or have another shape to increase frictional or mechanical resistance against movement and enable a locking mechanism to join the ends of the one or more rings of the implant device. FIG. 8A is a view from the front of the distal ring or proximal ring of implant device 100 or 100' where the ends of the ring(s) are lap jointed. Here, the ends of the rings overlap in a lap joint 40.

Figure 8B:
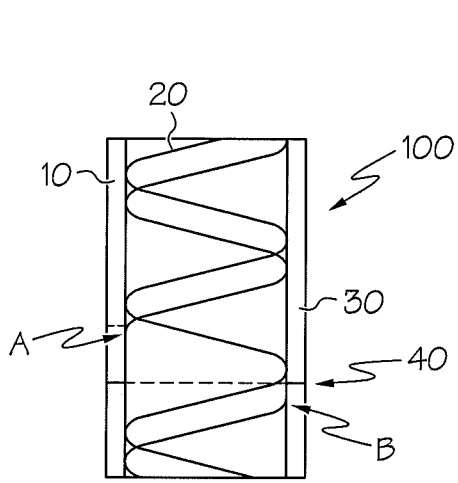
FIG. 8B is a side/top view of a an embodiment of a multi-substrate implant device with stabilizer element having an overlap, according to aspects of the inventive concept.

FIG. 8B shows a side or top view of implant device 100 of FIGS. 1 and 4 with lap joint 40. Stabilizer element 20 is disposed between the rings 10, 30. Here, as an example, stabilizer element 20 as an end A that terminates on ring 10 and another end B that terminates on ring 30. However, the inventive concepts are not inherently limited to such termination points or approaches. The stabilizer element does not have to terminate on a ring.

Figure 8C:
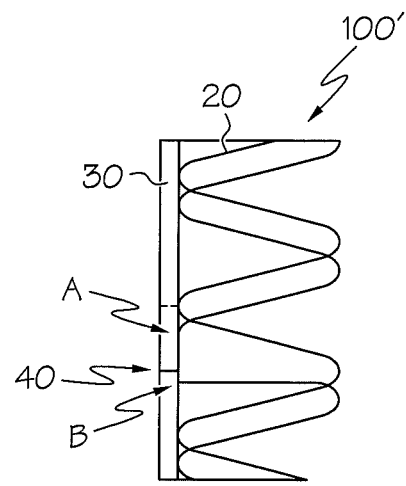
FIG. 8C is a side/top view of a an embodiment of a single-substrate implant device with stabilizer element having an overlap, according to aspects of the inventive concept.

FIG. 8C shows a side or top view of implant device 100' of FIGS. 2 and 3 with lap joint 40. Stabilizer element 20 laterally extends from ring 30. Here, as an example, stabilizer element 20 as an end A that terminates on ring 30 and another end B that also terminates on ring 30. However, the inventive concepts are not inherently limited to such termination points or approaches. The stabilizer element does not have to terminate on a ring.

Variations

The implant may be permanent, removable, or the same may be configured and designed to be absorbed into the body after a period of time. In a removable embodiment, a removable portion (which may be the entire implant or a portion thereof) may be installed for a period of time, e.g., between 30 minutes and 24 hours, and then removed. During this time, the device may impart pressure against the tissue, necrosing the same and rendering the local tissue electrically inert, thereby creating a block. While the procedure and device have been described in the context of the PVs, the same may be conveniently employed in the coronary sinus as well. Other potential treatment sites include the IVC, SVC, coronary sinus, and the vein of Marshall, as well as other vessels and electrically-viable substrates. In addition, the implant device may be employed to invoke a neurological response of the ganglion plexus.

Other implementations of the implant device may include one or more of the following. The device may include a contiguous circumferential ring substantially normally perpendicular to the ostium of the PV, and the ring-shaped implant device may have at least 1 full rotation, where a second ring e.g., proximal ring 10) in a double ring embodiment can have a pitch that is >1° from the first ring (e.g., distal ring 30).

The implant device can provide radial support to stenosed vessels, such as a stenosed PV. The implant device may have a distal ring 30 and a proximal ring 10, the distal ring 30 can be deployed at the distal end of the electrically active PV sleeve that extends within a human PV. The proximal ring 10 can be deployed at the proximal end or ostia of the PV and employ a single extension arm or a plurality of extension arms, as one or more stabilizer elements that extend distally toward and connect to the distal ring. The stabilizer element that joins the distal and proximal rings may be designed to interrupt ectopic electrical signals emanating from within the PV.

Figure 9:
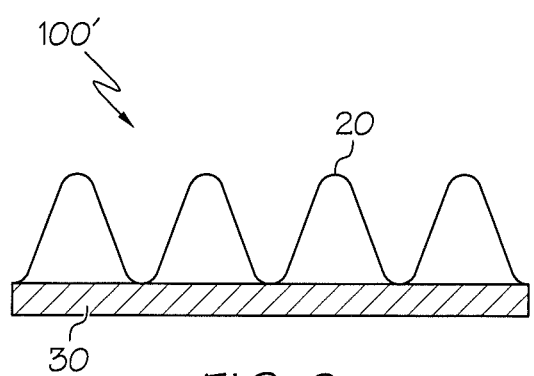
FIG. 9 is a side/top view of a single-substrate implant device with stabilizer element having an overlap having a treated surface, according to aspects of the inventive concept.

The implant device may be implanted within a vessel of the heart and may generate circumferential radial pressure sufficient to block the cellular exchange of sodium and/or sodium and calcium or potassium from entering the cell, thus rendering the cell electrically inert. The implant device may apply mechanical pressure to cardiac tissue causing focal apoptosis/necrosis. The implant device may have a material composition, surface treatment, coating, or biological agent and/or drug to cause a human biological response, e.g., intimal hyperplasia or endothelization, in a controlled or semi-controlled way in order to effect a long-term electrical block at or within the PV or other electrically active vessels or structures within the heart. Such a surface treatment can be as shown in FIG. 9, where distal ring 30 of implant device 100' includes a surface treatment 32 (e.g., coating and/or texturing).

The implant device may have at least one full circumferential winding, and indeed more, and may include a helical extension moving distally from the outer diameter of the first ring and terminating within the vessel to prevent migration of the implant device. The implant device may have various cross-sectional shapes designed to focus mechanical force in a circumferential or helical pattern against the inner surface of a vessel or structure within the heart. These shapes include, but are not limited to, round or circular, triangular, rectangular, "U"-shaped, or any number of other shape combinations. The implant device may have a material composition and/or geometry designed to sufficiently conform to tissue to prevent coagulation or thrombus, and may include a material coating to further reduce or prevent such coagulation or thrombus, such as surface treatment 32 shown in FIG. 9, as an example.

In some implementations, the implant device may act as an electrical wave reflector, changing the course of the electrical wave back to its origin and in some implementations acting as a cancellation medium to electrical waves emanating from the source. The implant device may have a circular, oval, hexagonal, pentagonal, and/or octagonal shape when viewing in an end view, formed around a central axes X (see FIG. 7). This geometric shape may be designed to improve conformability to the vessel following implantation. In this regard, it is noted that approximately 30% of PV's have an oval shape. By changing the geometry of the implant device, the implant device and vessel may be mutually conformed, and the radial force equalized along the circumference of the inner surface of the PVs. The implant device may have the above-noted shapes at the proximal end, but may employ a circular shape at the distal end. The implant device may be employed in combination with an implantable cardioverter-defibrillator (ICD) to deliver currents or voltages to heart tissues. (Such devices may be coupled to an ICD in a wired fashion or wirelessly. Other devices that may take advantage of the convenient placement of the implanted devices may similarly benefit from coupling to the same.

Deployment Catheters

An implant device according to aspects of the inventive concepts may be deployed in various ways.

Figures 10A, 10B:
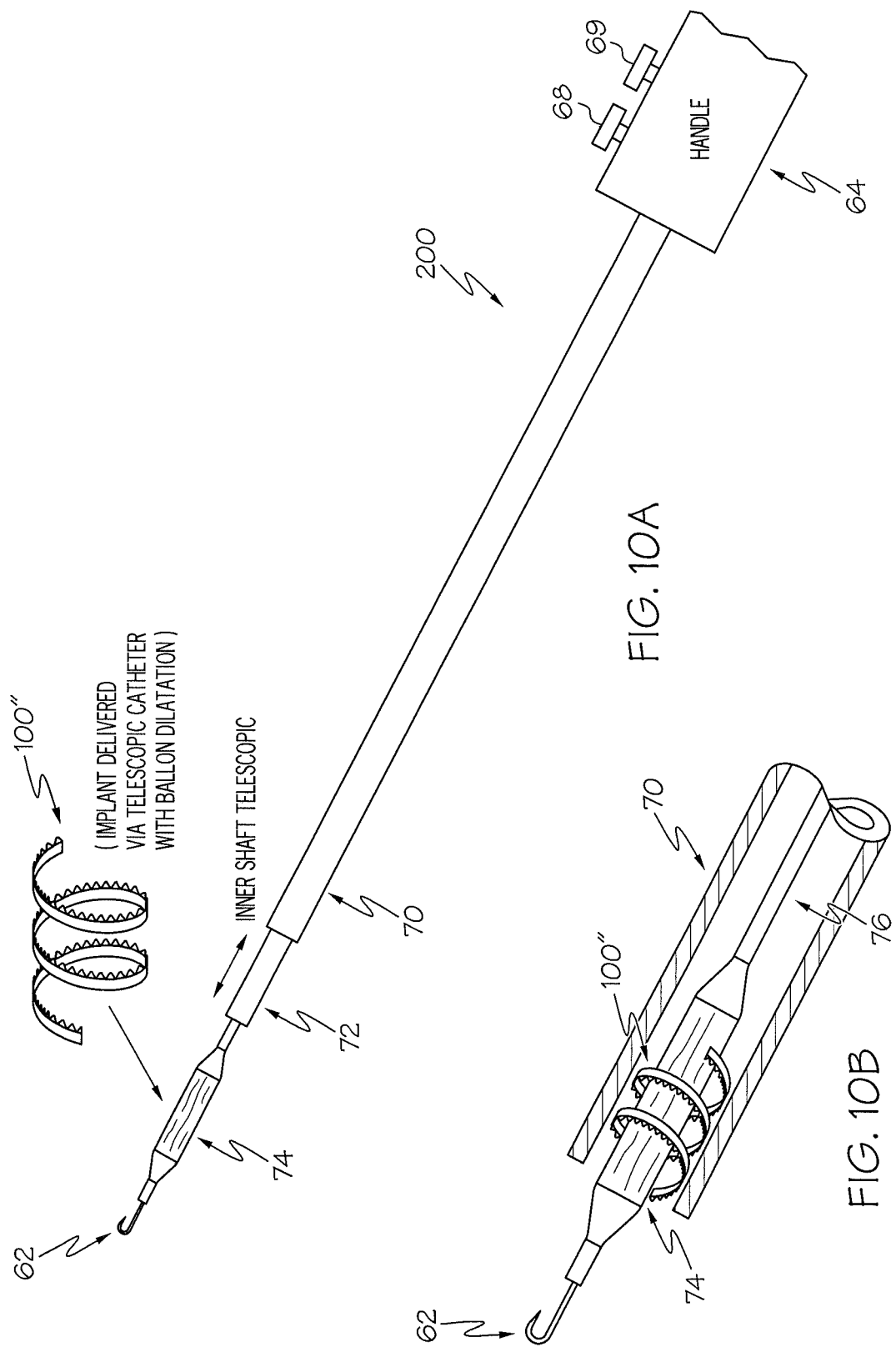
FIG. 10A is a side view of an embodiment of a delivery catheter for use with an implant device with stabilizer element, according to aspects of the inventive concept.
FIG. 10B is a scaled up side view of a portion of the delivery catheter of FIG. 10A with the implant device with stabilizer element retracted, according to aspects of the inventive concept.

In one implementation, illustrated in FIGS. 10A-B, a delivery catheter 200 takes the form of a telescopic catheter. As is shown in the embodiment of FIG. 10A, the catheter 200 has a handle 64 attached to an outer sheath 70. A telescoping inner shaft 72 moves within the outer sheath 70 to help deploy a catheter distal end delivery portion 74, which could be a balloon portion or a similar device, such as an expandable basket, that can be controllably expanded to deploy the implant device. In some embodiments, the distal end delivery portion 74 need not be expandable, particularly if the implant device is biased to expand when unconstrained through the use of a memory material. The delivery portion 74 is attached to a guide wire 76, that can be controlled by a know 68 at handle 64. An implant device 100" (or 100 or 100') can be compressed (or tightly wound) to obtain a small cross-sectional profile sufficient for deployment. Once at a target location, the delivery portion can be expanded to transition the implant device 100" to a deployed, uncompressed state. FIG. 10B shows the delivery portion 74 with the un-deployed implant device 100" residing within outer shaft 70, and attached to controllable guide wire 76.

In the above implementation, the design includes a spiral or pig-tail end that allows the implant to be delivered in a controlled manner and which protects the endocardial surface of the vein. In this embodiment, at a distal end, the delivery catheter 200 includes a PeBax® (or other material) loop or pigtail 62. The distal end of the delivery system may be employed for diagnostic purposes, such as ECG mapping of the vein prior to and after implanting the implant device using the electrodes. The distal end may also allow a user to recapture the implant using devices described below if it is partially or already deployed, enabling further control and proper placement within the PVs.

In this embodiment, the implant device 100" has a helical shape and is in an un-deployed configuration, but in other embodiments, the implant device could be a ring-shaped implant device, such as implant device 100 or implant device 100' shown above, as examples. The implant device may extend through the pigtail 62 and may further extend a short distance from the distal end of the pigtail during deployment. The distal end of the delivery system may also include a design where the catheter distal end is in a straight or neutral position and then steered using knobs 68 and/or levers on the handle 64 to create the pigtail 62 distal segment. Another lever 69 located on the handle 64 may be employed to deflect or steer the distal segment for cannulation of each pulmonary vein. This design may also include a plurality of electrodes to enable intra-cardiac electrogram interpretation.

By pushing the implant device out of the distal end of the catheter, the same may take up a position within the PV at a target location, as desired. One purpose of the PeBax pigtail 62 is to protect the vein during deployment in the same way, e.g., as a Lasso® catheter does. The pigtail and/or distal delivery portion (e.g., a balloon segment) could also expand the vessel prior to deployment of said implant device, such that radial and lateral expansion of said vessel occurs so the deployment of said implant device is not inhibited, then the pigtail and/or distal delivery portion (e.g., a balloon like device) is then deflated such to then allow tissue to contact said implant. This method could reduce the load seen on implant to simplify deployment and improve safety. In addition, the PeBax pigtail 62 may be equipped with electrodes to allow mapping and/or ablation, as described in greater detail below. The pitch of the distal loop or pigtail may be altered in known manner, e.g., by the guide wire 76, to allow different cardiac geometries to be accommodated. Where mapping electrodes are used, their length may range from approximately 0.5-4.0 mm, as an example. In various embodiments, portions of the delivery catheter 200 may include or constitute a Tuohy-Borst hemostasis valve or adaptor.

In various embodiments, a rectangular lumen may be employed to contain and deliver the implant and a circular or oval lumen may be employed to contain signal wires for mapping and ablation electrodes. Of course, it will be understood that the shape of the lumens may vary. In this way, mapping may be accomplished prior to deployment of the implant into the vein, e.g., allowing for acute block measurement. Of course, the signal block may not happen acutely in some patients, instead requiring prolonged exposure to the implant. In addition, it will be understood that more than one rectangular or circular lumen may be employed, and their shapes may differ, according to the needs of any given catheter design. In systems where the catheter is made fully steerable or deflectable, additional lumens may be employed to provide the necessary control wires for steering or deflection.

In some embodiments, the delivery catheter 200 may include other variations. For example, the catheter may include a grabber or grip 130, e.g., a toothed grip, configured to grab and hold the implant device. As an example, laser (or other) cuts and may be made in a distal cylindrical catheter tip to form a mouth or grip, which may be used to grab a proximal end of the implant device. The laser cuts can be made radially or longitudinally to the cylindrical axis of the grabber. It will be understood that curved cuts may also be employed, according to the needs of the particular application. The cuts allow bending or flexing away from the remainder of the grabber. The mouth or grip may be configured, e.g., via heat treatment (e.g., using a memory metal such as Nitinol) or design or both, to distend or open when the mouth or grip is not confined by the outer sheath 70. Once the same is thus extended away from the outer sheath 70, the same may open and release the implant.

In a related implementation, the implant device may be formed with a groove between elements or other feature to allow the grabber to hold the same in a secure and/or locked fashion. Similarly, the grabber may have formed thereon a "tooth" between upper half and lower half to allow additional points of contact. The implant device may also be configured with scalloped ends employed for this purpose.

In any case, when the grabber navigates through the sheath 70 or delivery catheter, it must navigate both curved sections and straight sections. In some systems, it may be advantageous to provide the same with a small curve or with additional laser cuts to allow the grabber device a degree of flexibility.

Figure 11A:
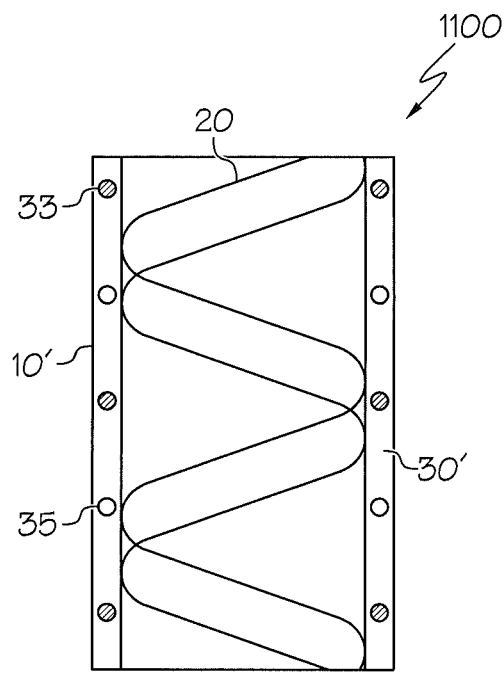
FIG. 11A is a side/top view of a an embodiment of a multi-substrate implant device with stabilizer element having electrodes, according to aspects of the inventive concept.
Figure 11B:
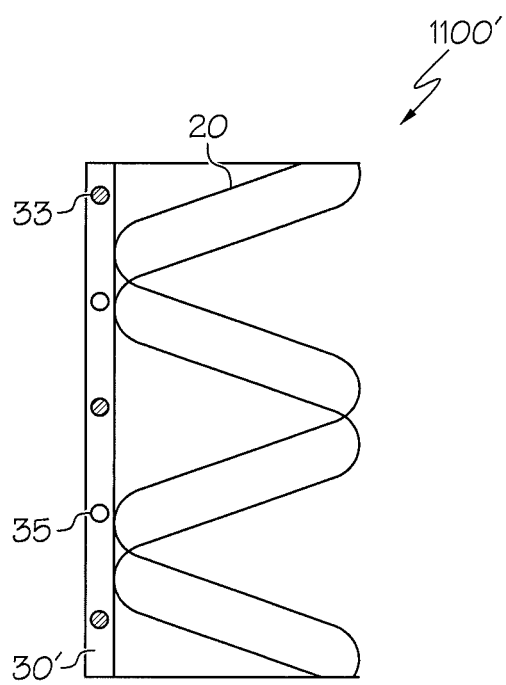
FIG. 11B is a side/top view of a an embodiment of a single-substrate implant device with stabilizer element having electrodes, according to aspects of the inventive concept.

Ablation with Delivery Catheter Device, Including with Partial Deployment of the Implant Device Referring to the embodiments of FIGS. 11A and 11B, an implant device 1100, 1100' may include ablation device and/or a mapping device integral with or provide in conjunction with a proximal ring 10' and a distal ring 30'. The distal ring 30' may provide both an anchoring aspect and a mapping aspect. In particular, the distal ring 30' may incorporate a number of mapping electrodes 33. The proximal ring 10' may incorporate a number of ablating electrodes 35. The distal set may enter into a pulmonary vein and become temporarily apposed to the inner lumen therein. In this sense, the implant device 1100, 1100' with two sets of electrodes 33, 35 may be disposed similarly to the implanted device discussed above, but in this case, the same would be retracted after treatment.

The distal ring 30' employs its electrodes for mapping, while the proximal ring 10' may employ its electrodes 33, 35 for mapping and/or ablation. The apposed electrode of the distal ring 30' may be as noted above, and while the same may become lodged with respect to translational displacement, the same may also be easily rotated with respect to a track formed by the pressure of the ring against the tissue of the pulmonary vein. The proximal ring 10' electrodes may then contact the ostium and via RF ablation cause necrosis of a ring of tissue around the ostium.

In this system, even without steering, an effective lesion may be created by rotating the handle and ablating, resulting in a consistent and repeatable lesion that may be created safely. As the same spot is returned to in the ostium, or nearly returned to, by the electrode, or electrodes, a relatively closed-shape lesion is formed and the possibility of micro-reentrant currents is significantly reduced or eliminated.

It will be noted that, in various embodiments, it is not necessary for there to be two separate rings—a continuous set of electrodes may be provided, e.g., to accommodate varying sizes of vessels and cardiac features, and selective electrode activation may be employed to map and/or ablate desired tissue.

In another implementation, an implant device as described may be deployed so as to gain purchase in the PV, e.g., via a partial deployment. The electrodes on the catheter or sheath may be provided and then revolved around the vein by rotating the handle while ablation is conducted at a plurality of locations. In this way, a well-defined circular lesion may ensue, and block may be tested for during the procedure. In this regard, it is noted that one or multiple electrodes may be activated at any one time or during any one procedure. In addition, the user can define circular lesions (by rotating the entire system) or helical lesions (but slowly extending portions of the ring device from the sheath, and revolving the sheath (but not ring device) in so doing). If multiple electrodes are activated while creating a helical lesion, then one can achieve multiple helical lesions, which have in some cases been found particularly useful for atrial fibrillation treatment.

Moreover, following ablation and/or mapping, the implant device may be fully implanted in the vein as described elsewhere. Of course, in some implementations, the implant device may also be pulled back into the catheter or sheath.

In a related implementation, the system may employ a small device, i.e., a ratchet sleeve having a cylinder and extension, within the delivery catheter or sheath 70 that can provide a ratcheting function. In this way, the handle 68 may be simplified, and provided with greater control, by having the operator only have to provide a repeated short-stroke motion to controllably cause the implant device to exit the sheath 70 and become implanted in the body. In particular, the ratchet sleeve can be disposed within the sheath 70. The implant device can be prevented from retracting into the sheath 70 by virtue of the ratchet sleeve.

In a further related embodiment, a small delivery portion 74 (e.g., a balloon portion) may be inflated within the ratchet sleeve if desired to provide a way for the ratchet sleeve to grab onto the implant device. By placing a tip of the implant device, e.g., the proximal tip, into the ratchet sleeve, and inflating the delivery portion 74 to fill up the interstitial space, the implant device may be effectively grabbed by being held between the delivery portion 75 and the wall of the ratchet sleeve.

In another embodiment, the inflation lumen and delivery portion 74 may be provided in a pusher, and the implant device may be grabbed by inserting the pusher into the ratchet sleeve and inflating a balloon or other expandable delivery portion 74, thereby constricting the implant tip in the same small diameter as the delivery portion (within the ratchet sleeve), causing the same to be grabbed. In yet another embodiment, a small balloon or other expandable delivery portion 74 may be employed to render the volume within the ratchet sleeve closed, and in that case a small negative pressure may be pulled on the interior of the ratchet sleeve, constricting its walls and causing the same to pull inwards, grabbing onto the implant device in the process.

In an alternative embodiment, the implant device is a ring-shaped implant device 100, 100', disposed around a threaded mandrel and confined by an outer tube. Removal of the outer tube allows the implanted device to spring away from the mandrel by virtue of its shape-memory character, e.g., the implant device can have a memory shape that biases the device into an expanded, uncompressed state. In general, removing the outer tube causes immediate deployment, resulting in impingement of the implant device 100, 100' against a vessel wall.

In another embodiment, the deliver catheter 200 may be configured to deploy the implant device perpendicularly to the direction of implantation. This deployment direction may be useful in certain patient anatomies.

In various implementations, the implant device 100, 100' may be deployed from the proximal side first, such as at the ostium of the atrial/vein junction, followed by deployment of the distal ring within the vessel. The reason this can be advantageous is that this can allow more mechanical force to be applied to the luminal surface of the myocardial sleeve. In particular, the first ring, e.g., proximal ring 10, may be disposed in the ostial/atrial junction location, implanted, and the stabilizer element 20 and second ring, e.g., distal ring 30, may then be unwound or expanded into the PV. This unwinding or expanded deployment allows installation of an implant device that can provide sufficient mechanical force to achieve the clinical response necessary, e.g., as well as inactivation of the Na-channels, causing dehydration of the cells by compression, resulting in optimal clinical result.

It is noted in this embodiment of a set of rings, connected by stabilizer element, the implant device may not be initially sized for the vein, but allowed the implant device to simply expand, such as by the effect of the shape memory alloy. However, this may, in certain cases, not provide the needed mechanical force to compress the surface cells. In addition, during deployment, e.g., while the implant device is partially deployed, the action of the partial implant on the electrical signal propagation may be confirmed or verified.

To deploy the distal end first, a split catheter shaft may be employed, such that separation of the catheter shaft at a location near the distal end causes the distal end to be deployed first. Of course, in certain implementations, the proximal end may also be deployed first. Such a split catheter shaft may be employed, e.g., in the delivery of the implant device. In this embodiment, the distal end of the delivery catheter 200 may employ a polymer tip for atraumatic delivery, and the polymer tip may be radiopaque. As in most of the embodiments described herein, the implant device may be delivered via a guide wire 76.

In general, the delivery catheter 200 will have distal and proximal ends, where the distal end employs an atraumatic distal tip and the proximal end includes a handle 64. The delivery catheter 200 can further include a catheter shaft having a tubular or other geometric shape catheter structure traversing from the proximal end to the distal end. The guide wire lumen includes a luminal space to enable passage of a range of guide wire sizes. In one embodiment, the guide wire lumen is furthermore capable of being advanced distally or proximally to enable deployment of the implant device attached along the external surface of the guide wire lumen and contained within the inner surface of the outer catheter sheath 70. As in some embodiments above, the delivery catheter 200 may employ a flexible distal segment and a steering wire 70 anchored at the distal portion of the delivery catheter.

In some embodiments, the deployment catheter, or another device, may allow a degree of recapture to occur in order to fix incorrect implanted device placements within the PV, or other locations. For example, where the implant device is pushed through a tube for deployment, the same two may be used to deliver a small wire equipped with maneuverable jaws (gripper) at its distal end. In some cases, for example, a modified guide wire may be employed. In the same way, a ratchet sleeve with incorporated balloon or other expandable delivery portion, as examples, may provide this function as well.

Multiple ring devices may be delivered in a single surgical operation, such as in the four pulmonary veins in a given patient. For example, in such a procedure, an MRI may be employed initially in order to determine sizes of the various pulmonary veins. According to the order the physician intends to use for deployment, suitable rings may then be loaded into the device. For example, the physician may intend a plan of treatment in a clockwise direction starting with the left superior pulmonary vein (LSPV), followed by the left inferior pulmonary vein (LIPV), followed by the right inferior pulmonary vein (RIPV), followed by the right superior pulmonary vein (RSPV). The device efficacy may then be verified by performing a mapping maneuver in each vein. That is, a conduction block may be verified following deployment, such as by using the mapping capability described in this specification. It is believed to be a particularly beneficial advantage that multiple implant device deployment and verification may be achieved using a single "stick" through the septum. The above procedure of deployment may only require, e.g., 15 to 20 minutes.

Alternative Implant Device Examples

Figure 11C:
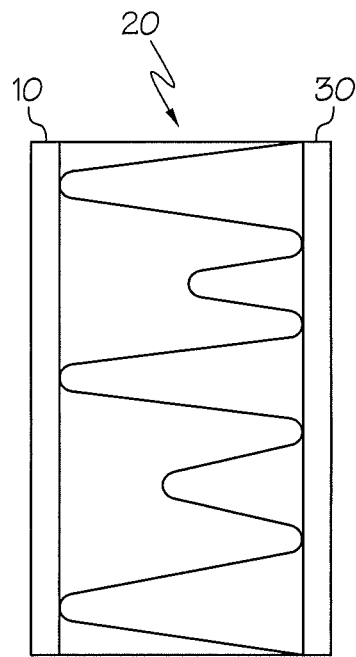
FIG. 11C shows an embodiment of a double-substrate implant device with a stabilizer element having full peaks and less than full peaks, in accordance with aspects of the inventive concepts.
Figure 11D:
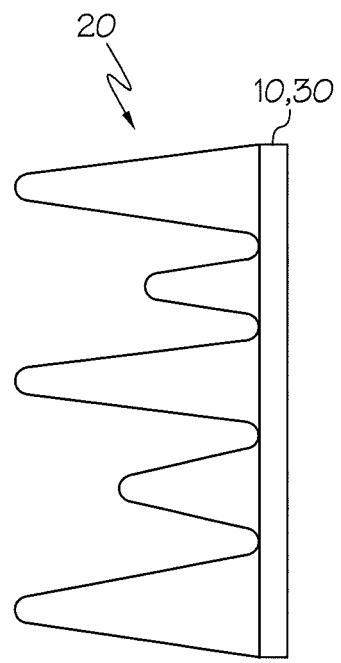
FIG. 11D shows an embodiment of a single-substrate implant device with a stabilizer element having full peaks and less than full peaks, in accordance with aspects of the inventive concepts.

FIGS. 11C-11J show different embodiments of single-substrate and double-substrate implant devices, in accordance with aspects of the inventive concepts. FIG. 11C shows an implant device having two substrates 10, 30 and a stabilizer element 20 having full peaks and less than full peaks, that do not span the full width of the stabilizer element 20. FIG. 11D shows an implant device having a single substrate 10, 30 and a stabilizer element 20 having full peaks and less than full peaks, that do not span the full width of the stabilizer element 20.

Figure 11E:
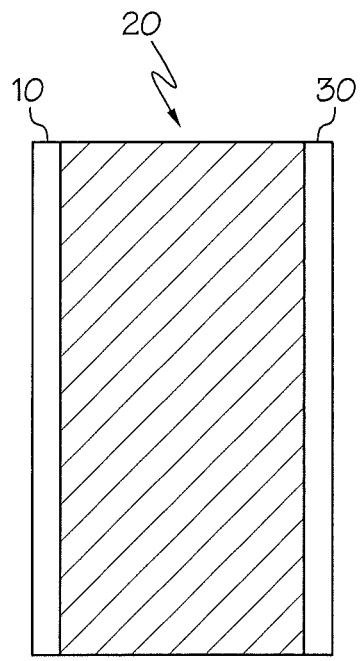
FIG. 11E shows an embodiment of a double-substrate implant device with a stabilizer element having a slanted orientation, in accordance with aspects of the inventive concepts.
Figure 11F:
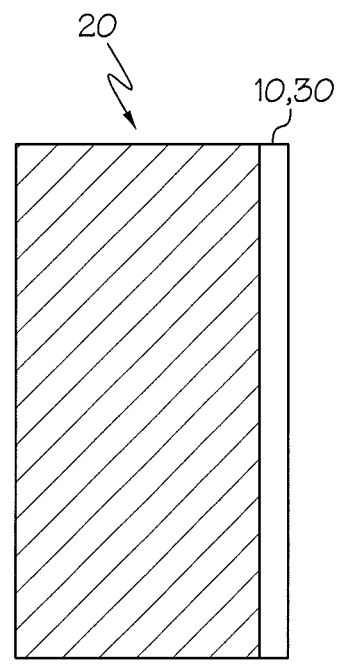
FIG. 11F shows an embodiment of a single-substrate implant device with a stabilizer element having a slanted orientation, in accordance with aspects of the inventive concepts.
Figure 11G:
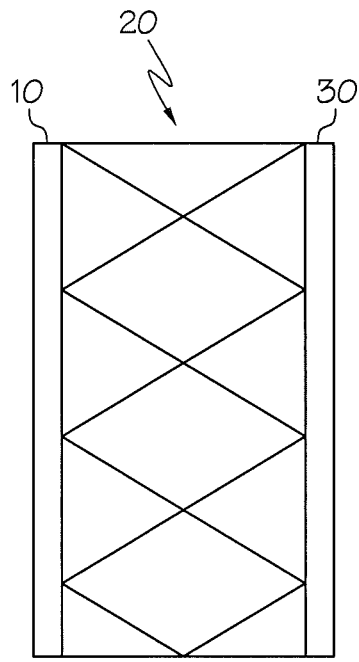
FIG. 11G shows an embodiment of a double-substrate implant device with a stabilizer element having crossing wires, in accordance with aspects of the inventive concepts.
Figure 11H:
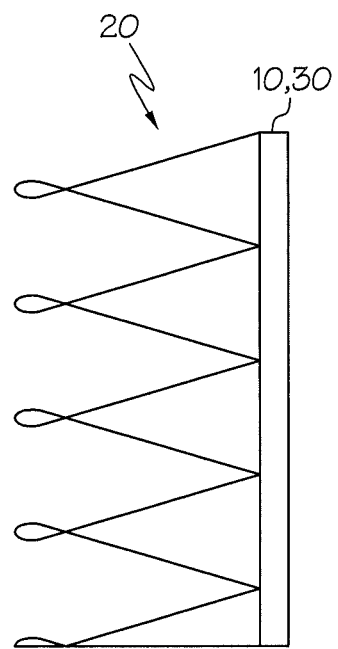
FIG. 11H shows an embodiment of a single-substrate implant device with a stabilizer element having looped ends, in accordance with aspects of the inventive concepts.

FIG. 11E shows an implant device having two substrates 10, 30 and a stabilizer element 20 having slanted wires. FIG. 11D shows an implant device having a single substrate 10, 30 and a stabilizer element 20 having slanted wires. FIG. 11G shows an implant device having two substrates 10, 30 and a stabilizer element 20 having crossed wires. FIG. 11H shows an implant device having a single substrate 10, 30 and a stabilizer element 20 having angled crossed wires.

Figure 11I:
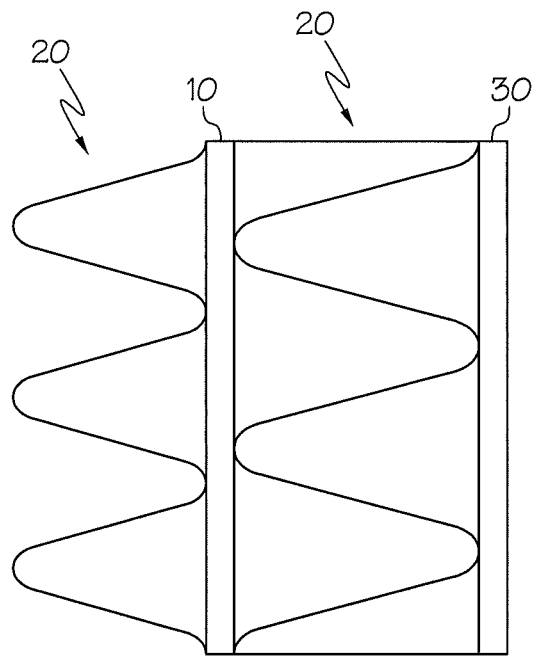
FIG. 11I shows an embodiment of a double-substrate implant device with a two stabilizer elements, in accordance with aspects of the inventive concepts.
Figure 11J:
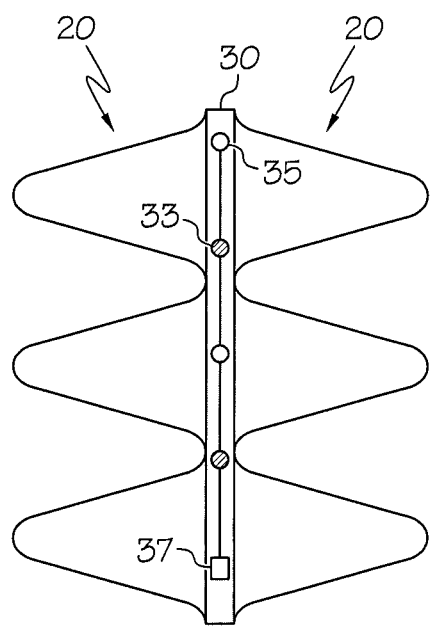
FIG. 11J shows an embodiment of a single-substrate implant device with a two stabilizer elements, in accordance with aspects of the inventive concepts.

FIG. 11I shows an implant device having two substrates 10, 30 and two stabilizer elements 20. FIG. 11J shows an implant device having a single substrate 10 and two stabilizer elements 20. In this embodiment, substrate 30 includes electrodes 10, 30 and a circuit 37 coupled to the electrodes for monitoring and/or control thereof.

Deployment Examples

Figure 12A:
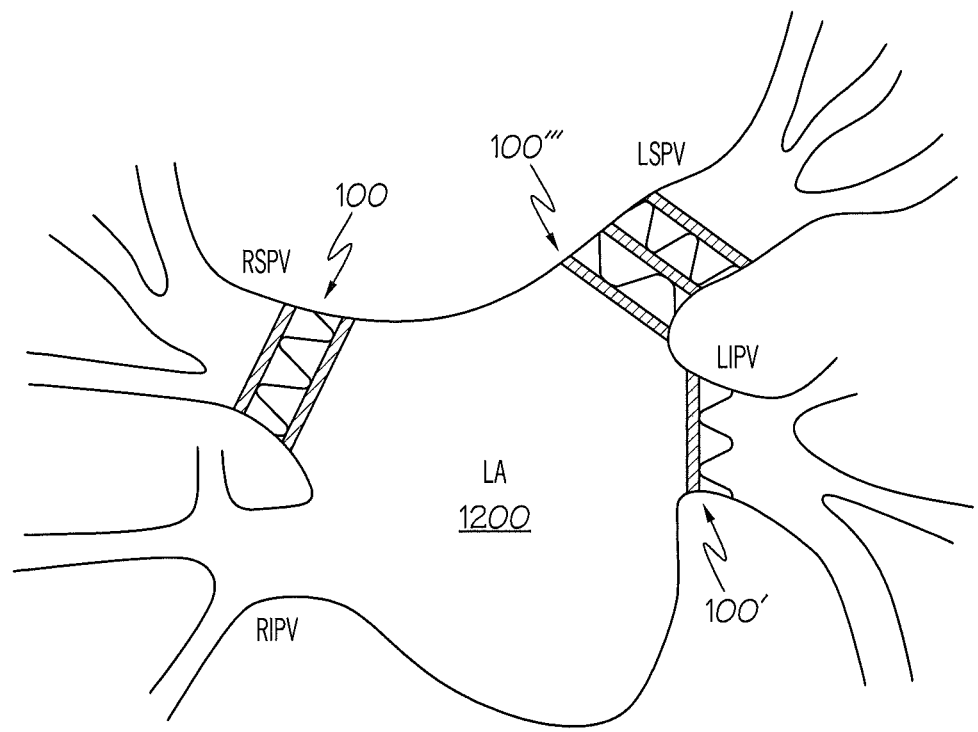
FIG. 12A illustrates an embodiment of a heart having a plurality of implant devices deployed within different vessels, according to aspects of the inventive concept.
Figure 12B:
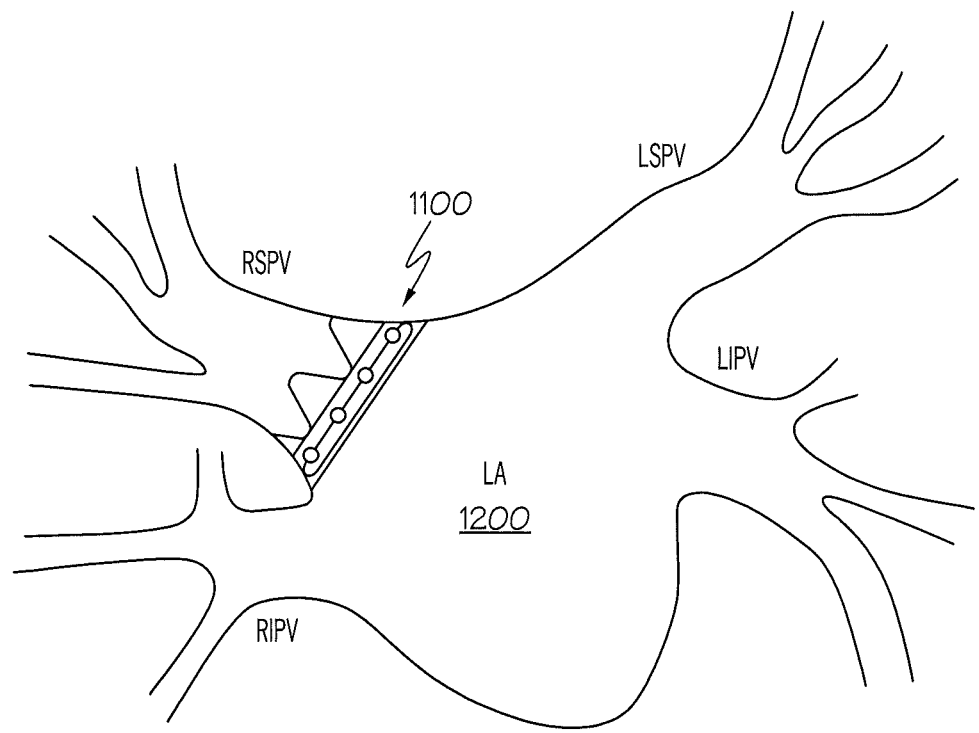
FIG. 12B illustrates another embodiment of a heart having a single implant devices deployed within different a vessel, according to aspects of the inventive concept.
Figure 12C:
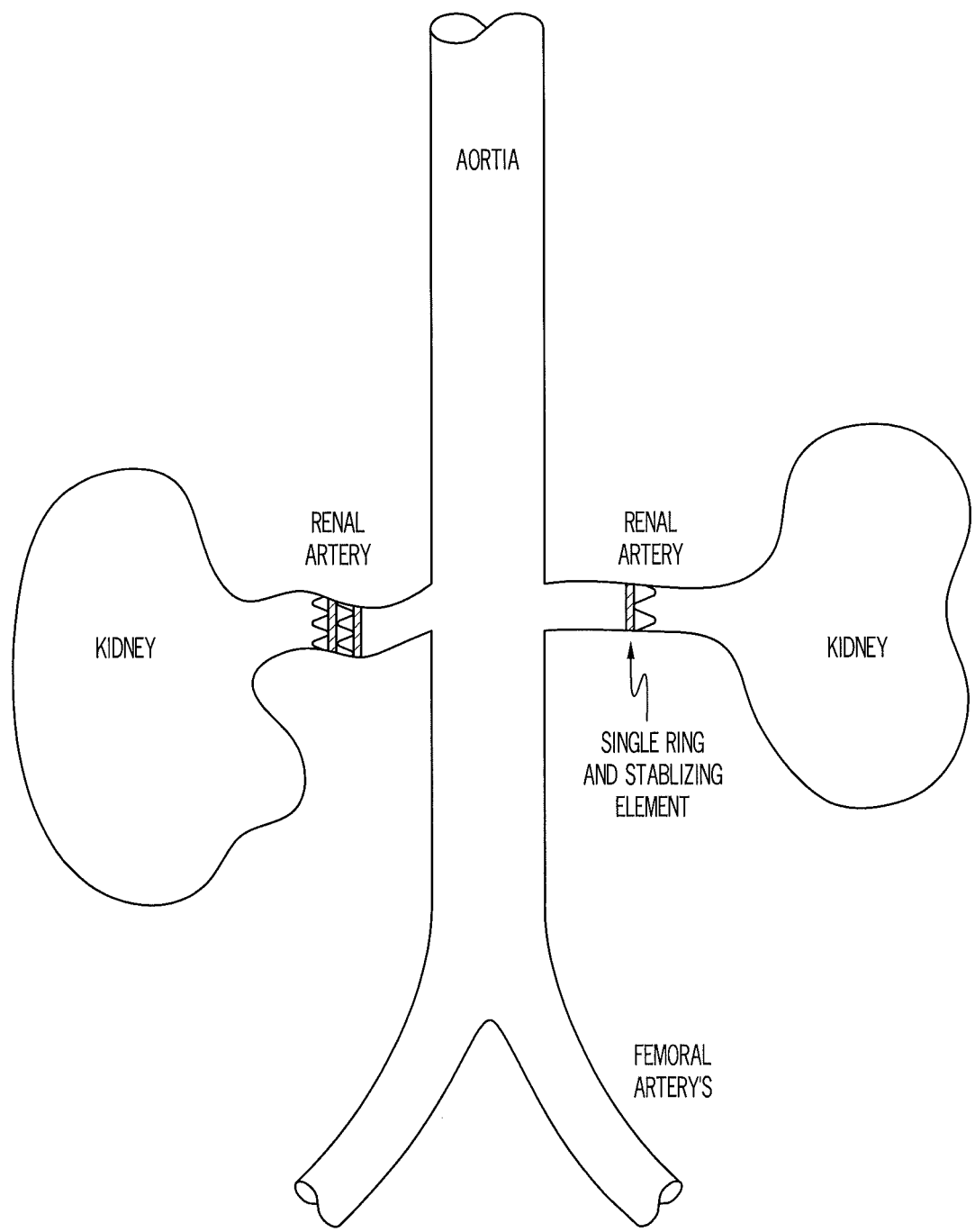
FIG. 12C illustrates an implant device with stabilizer element deployed within another vessel, e.g., a renal artery, according to aspects of the inventive concept.

FIGS. 12A-12C shows schematic views of different embodiments of implant devices, in accordance with aspects of the inventive concepts, deployed in different cardiac vessels. In particular, FIGS. 12A-B illustrate an implant device with stabilizer element deployed within a vessel, e.g., a pulmonary vein, according to aspects of the inventive concept. Referring to FIG. 12 A, an implant device 100 having two substrates 10, 30 and an intermediate stabilizer element 20 is deployed in the right superior pulmonary vein (RSPV). A second implant device 100' is deployed in the left superior pulmonary vein (LSPV), which has three substrates (or rings) separated by two intermediate, laterally protruding stabilizer elements. And a third implant device 100' is deployed in the left inferior pulmonary vein (LIPV) having a single substrate (or ring) and a laterally protruding stabilizer element.

Referring to FIG. 12B, an implant device 1100 having a substrate with electrodes (e.g., electrodes 33 and/or electrodes 35) and an intermediate stabilizer element 20 is deployed in the right superior pulmonary vein (RSPV).

FIG. 12C illustrates an implant device with stabilizer element deployed within another vessel, e.g., a renal artery, according to aspects of the inventive concept. Here, two different implant devices are deployed. A first implant device having two substrates and two laterally protruding stabilizer elements are shown in the pulmonary vein to the left. And a second implant device having a single substrate and one laterally protruding stabilizer element is shown in the pulmonary vein to the right.

In various embodiment, when a substrate is shown with shading this can indicate a treated surface, as described above, e.g., roughening or coating.

Mechanism of Operation

An implant device according to the inventive concepts, e.g., a single-ring implant device, a double-ring implant device, or a helical implant device may be configured to compress tissue, stopping the propagation of hyperplasia proliferation associated with pulmonary vein stenosis, hypertension and or atrial fibrillation in a manner disclosed below. The implant device may be configured to necrose the surrounding tissue, which can cause a narrowing of certain channels within the tissue associated with the propagation of aberrant electric signals. For example, sodium, calcium, or potassium channels may be blocked by mild compression as provided by the implant device in accordance with aspects of the inventive concepts. It is believed that a suitable amount of force will result in a compression of the first one to five cellular layers in the tissue. In particular, it may be important to at least compress the first layer. Using such an implant device and method, PV isolation may be achieved without means of an energy source or surgical procedure.

It is believed that the amount of pressure necessary should be more than 0.5 grams per square millimeter, but less than 300 grams per square millimeter, e.g., less than about 200 grams per square millimeter, as noted above. While it may be desired to have the implant device exert a relatively constant force around the circumference of the vein, it is more likely, given anatomical imperfections, that certain areas will receive more pressure than others. However, compliance of the implant device helps to distribute forces around the inner surface of the vessel or vein. In general, it is believed that the amount of pressure needed will primarily be a function of the material used, the diameter of the artery or vein, and the thickness of the muscle sleeve.

It is noted that the implant device, e.g., the distal ring inside the vessel, may perform an anchoring function as well as a conductive or neurological delay function. Moreover, it is noted that a full conductive signal block is not necessary, nor is full transmurality needed. In some cases, merely a slowing down of the net signal propagation may be enough to be clinically effective. For example, a 50% improvement in vessel patency may be highly significant in stopping the propagation of pulmonary vein stenosis. In any case, the device's geometry, roughly matching the myocardial sleeve, further enhances this effect. If the configuration of the implant device, e.g., ring, is such that these are disrupted, then the disruption can act as an efficacious treatment per se. Such disruptions may be particularly effected by the stabilizing elements between the rings, for example. It is also noted that the ring or rings inside the PV allows for a therapeutic treatment modality in the vein, but without the serious complications associated with prior devices, RF or cryogenic in-the-vein treatments, or the like.

It is also noted that the ring or rings may cause the vessel in which it dwells to become more oval or round, or otherwise to maintain a more open shape than that which it adopted before, in the absence of the implant device. In this way, the implant device acts similar to a stent, enhancing hemodynamics and the resulting blood flow. The device affects the shape of the vein, and vice-versa. This effect improves apposition of the implant device to improve outcomes by enabling circumferential contact resulting in conduction block, laminar blood flow, and can help to treat stenotic vessels. One aspect of the implant device that assists in this regard is the device ring compliance, which causes the device to conform to the vessel—i.e., the radial expansion helps to keep the implant device in place in a dynamic way, which current PV stents generally cannot. In some cases, the implant device may be specifically installed to perform the function of a PV stent, and if used in this way, generally, a stabilizer element may be employed between the two rings, or more. That is, if there are three rings, there may be a stabilizer element between each of the two rings.

It is noted that the above effect of the implant device has a multi-factorial response mechanism. First, is an acute response that, depending on implementation, may last from 1-45 days. After this, depending on the degree to which the deployed implant device has been treated, a secondary biological or chronic response mechanism may ensure long term safety as a result of the biological response to the implant, e.g., endothelialization, the same starting at 15-30 days and lasting indefinitely. The biological response of endothelization cell proliferation is designed to enable endothelial cells proliferation that are incapable of electrical cell-to-cell conduction. The treatment of the device refers to, e.g., the level to which the device has been roughened so as to act as an irritant to the adjoining tissue. The amount of endothelialization may be 'tuned' by this degree of roughening, which may occur via bead blasting, etc. The treatment may also be via surface modification, coatings, or the like. In FIGS. 5 and 9, as examples, the surface of one or more rings is treated by a coating or roughening, as indicated by the shading.

In some implementations, the metallic nature of the implant device may be employed to provide a level of active heating so as to heat or necrose tissue adjoining the implant. For example, such heating may be by way of chemical, chemical reaction, chemical reaction within blood of mammalian, induction using a device external to the patient. The device may be caused to heat the implant and thus heat (and treat) the tissue creating localized necrosis, and then be easily removed from the vicinity of the patient to stop the heating. In advanced versions of this embodiment, the heating device and the implant device may be tuned such that only one implant is heated at a time, if multiple implants have been deployed.

Construction

As will be understood, the substrate and stabilizer element may be constructed of several types of materials. For example, biocompatible metals such as Nitinol may be employed, and the same exhibit useful shape memory properties. Biocompatible polymers or elastomers may also be employed.

If the substrate, e.g., ring(s), is made of materials that are bioabsorbable, then the same may eventually be absorbed into the PV by virtue of the endothelialization, leaving only (and at most) a scar visible on the inside of the PV.

Coatings

While not required in all embodiments, various coatings or other agents may be applied or made part of the substrate(s) and/or stabilizer element(s), such coatings or agents capable of disrupting the propagation of aberrant electrical signals or otherwise treating arrhythmias. Such coatings may include drugs, biologics, chemicals, or combinations, and the same may cause some degree of necrosis that, by itself or in combination with the mechanical compression, acts as a treatment for arrhythmias. For example, a coating including alcohol may be employed as a sort of chemical ablation reagent. Such coatings may also enhance endothelialization, as discussed above. As another example, the substrate(s) and/or stabilizer element(s) may be coated with tantalum, e.g., a 3-5 micron coating.

Various illustrative implementations of the present invention have been described. However, one of ordinary skill in the art will recognize that additional embodiments are also possible and within the scope of the present invention.

Therefore, while the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

What is claimed is:

1. An implant device, comprising:
   at least one elongated substrate; and
   at least one stabilizer element laterally extending from an edge of the at least one substrate for a substantial portion of a length of the substrate,
   wherein the at least one stabilizer element has a zig-zag pattern comprising a plurality of peaks extending from the edge of the at least one elongated substrate and a plurality of valleys connected to the edge of the at least one elongated substrate, and
   wherein the at least one elongated substrate and the at least one stabilizer element are formed around a central axis of the implant device and the implant device is biased to radially expand away from the central axis from a constrained compressed to a deployed state when unconstrained, and
   wherein the at least one elongated substrate and the at least one stabilizer element have a helical coil shape forming a winding around the central axis.

2. The implant device of claim 1, further comprising:
   a micro-circuit configured to measure or monitor a value of electrical conduction propagating along an axis of a mammalian vessel within which the implant device is deployed.

3. The implant device of claim 2, further comprising:
   one or more electrodes disposed in or on the at least one substrate and in communication with the micro-circuit, the one or more electrodes configured for sensing conditions within the vessel and/or delivering energy to the vessel.

4. The implant device of claim 3, wherein the one or more electrodes include ablation electrodes, mapping electrodes, or ablation and mapping electrodes.

5. The implant device of claim 2, wherein the micro-circuit is configured to measure and/or monitor a value of electrical conduction propagating along the axis of the vessel.

6. The implant device of claim 5, wherein the micro-circuit is further configured to wirelessly transmit an indication of the electrical conduction in a mammalian vessel.

7. The implant device of claim 2, wherein the micro-circuit is configured to use an Ionic exchange with the vessel to charge a battery of the micro-circuit.

8. The implant device of claim 2, wherein the micro-circuit is configured to receive an electromagnetic signal and to inductively heat the vessel in response to the electromagnetic signal.

9. The implant device of claim 1, wherein the at least one elongated substrate and the at least one stabilizer element have a ring shape.

10. The implant device of claim 9, wherein at least one elongated substrate is a plurality of ring-shaped substrates.

11. The implant device of claim 10, wherein the at least one stabilizer element includes an intermediate stabilizer element and wherein the plurality of ring-shaped substrates comprises a first ring-shaped substrate and a second ring-shaped substrate maintained at a distance from each other by the intermediate stabilizer element, wherein the intermediate stabilizer element alternatingly connects to a plurality of points on the first ring-shaped substrate and a plurality of points on the second ring-shaped substrate.

12. The implant device of claim 11, wherein the intermediate stabilizer element has a zigzag pattern and maintain the first ring-shaped substrate and the second ring-shaped substrate substantially in parallel to each other.

13. The implant device of claim 9, wherein the implant device comprises a plurality of stabilizer elements.

14. The implant device of claim 1, wherein the implant device is configured to apply a substantially constant radial force against inner walls of a mammalian vessel at a target location in the deployed state.

15. The implant device of claim 14, wherein the substantially constant radial force has a magnitude sufficient to dilate the mammalian vessel at the target location.

16. The implant device of claim 14, wherein the unconstrained diameter of the implant device is at least 15% greater than a predetermined diameter of the mammalian vessel at the target location.

17. The implant device of claim 1, wherein the at least one elongated substrate comprises a plurality of substrates.

18. The implant device of claim 1, wherein the implant device comprises a plurality of stabilizer elements.

19. The implant device of claim 1, wherein the at least one stabilizer element comprises at least one wire stabilizer element.

20. The implant device of claim 1, wherein the implant device is configured to deliver a radial force against inner wall tissue of a mammalian vessel at a target location of between about 0.5 g/mm$^2$ and 300 g/mm$^2$ in the deployed state.

21. The implant device of claim 1, wherein the implant device is configured to deliver a radial force against tissue of a mammalian vessel at a target location that is sufficient to cause necrosis or apoptosis in the tissue in the deployed state, the necrosis or apoptosis sufficient to delay electrical, neurological signal conduction traveling along an axis of the vessel and/or within an adjacent chamber.

22. The implant device of claim 1, wherein the implant device is configured to deliver a radial force against tissue of a mammalian vessel at a target location that is sufficient to compress at least one Ion channel in the adjacent tissue sufficient to delay electrical or neurological signals traveling along an axis of the vessel and/or within an adjacent chamber.

* * * * *